(12) United States Patent
Kusters et al.

(10) Patent No.: US 11,137,344 B2
(45) Date of Patent: Oct. 5, 2021

(54) OPTICAL MIXING OF FLUIDS

(71) Applicant: Fenwal, Inc., Lake Zurich, IL (US)

(72) Inventors: Benjamin E. Kusters, Pleasant Prairie, WI (US); Kyungyoon Min, Kildeer, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 16/686,823

(22) Filed: Nov. 18, 2019

(65) Prior Publication Data

US 2020/0166451 A1   May 28, 2020

Related U.S. Application Data

(60) Provisional application No. 62/772,322, filed on Nov. 28, 2018.

(51) Int. Cl.
*G01N 21/25* (2006.01)
*G01N 21/31* (2006.01)
(Continued)

(52) U.S. Cl.
CPC ......... *G01N 21/255* (2013.01); *A61B 5/6866* (2013.01); *G01N 21/31* (2013.01); *G01N 33/49* (2013.01); *A61B 5/14535* (2013.01)

(58) Field of Classification Search
CPC .. B01L 19/527; B81C 1/00119; C12M 23/16; G01N 27/44791
See application file for complete search history.

(56) References Cited

U.S. PATENT DOCUMENTS 5,316,667 A    5/1994  Brown et al.
5,462,416 A   10/1995  Dennehey et al.
(Continued)

FOREIGN PATENT DOCUMENTS

WO    WO2017/018673 A1    3/2017

OTHER PUBLICATIONS

HemaXis "USPTO Patent Granted for Hemaxis Microfluidic Blood Collection Platform", Nov. 17, 2017, available at https://web.archive.org/web/20180810221355/https://hemaxis.com/uspto-patent-granted-for-hemaxis-microfluidic-blood-collection-platform/ links to https://www.youtube.com/watch?v=9vW0XfWDS68 (Year: 2017).*

(Continued)

*Primary Examiner* — Dominic J Bologna
(74) *Attorney, Agent, or Firm* — Cook Alex Ltd.

(57) ABSTRACT

A fluid to be optically monitored may be optically mixed to modify the apparent color perceived by a colorimetric optical sensor device. The fluid is positioned within a fluid compartment of a vessel also including a contrast compartment adjacent to the fluid compartment. The contrast compartment is configured to have a contrast color with a known main wavelength that is different from the main wavelength of the fluid color. Light from a broadband light source of the colorimetric optical sensor device is reflected off of the vessel, with the received light being received by an optical spectrometer. The optical spectrometer analyzes the received light to determine a main wavelength of the received light, followed by a controller determining a characteristic of the fluid, which is based on the main wavelengths of the received light and the contrast color and the percentage of the vessel occupied by the fluid compartment.

20 Claims, 16 Drawing Sheets

(51) Int. Cl.
*A61B 5/00* (2006.01)
*G01N 33/49* (2006.01)
*A61B 5/145* (2006.01)

(56) References Cited

U.S. PATENT DOCUMENTS

| | | | |
|---|---|---|---|
| 5,632,893 | A | 5/1997 | Brown et al. |
| 5,868,696 | A | 2/1999 | Giesler et al. |
| 5,980,760 | A | 11/1999 | Min et al. |
| 6,312,607 | B1 | 11/2001 | Brown et al. |
| 7,011,761 | B2 | 3/2006 | Muller |
| 7,297,272 | B2 | 11/2007 | Min et al. |
| 9,164,078 | B2 | 10/2015 | Min et al. |
| 9,833,557 | B2 | 12/2017 | Thill et al. |
| 9,895,482 | B2 | 1/2018 | Kusters et al. |
| 2003/0070969 | A1 | 4/2003 | Muller et al. |
| 2011/0149286 | A1* | 6/2011 | Wu ................... G01N 21/31 356/436 |
| 2013/0324815 | A1* | 12/2013 | Jian ................... G01N 21/474 600/327 |
| 2014/0057771 | A1 | 2/2014 | Case et al. |
| 2015/0219558 | A1 | 8/2015 | Koudelka et al. |

OTHER PUBLICATIONS iStockphoto "Group of Laboratory Equipment, Glass Erlenmeyer Conical Flask, Beaker and Test Tube filled with chemical liquid for a chemistry, stock photo", May 30, 2017, available at https://www.istockphoto.com/photo/group-of-laboratory-equipment-glass-erlenmeyer-conical-flask-beaker-and-test-tube-gm6 (Year: 2017).*

Jeon, Jinhyeok, et al. "SERS-based droplet microfluidics for high-throughput gradient analysis." Lab on a Chip 19.4 (2019): 674-681 (Year: 2019).*

Sun, Yuxi, et al. "Microfluidics technologies for blood-based cancer liquid biopsies." Analytica chimica acta 1012 (2018): 10-29 (Year: 2018).*

* cited by examiner

OPTICAL MIXING OF FLUIDS

CROSS-REFERENCE TO RELATED APPLICATIONS

This application claims the benefit of and priority of U.S. Provisional Patent Application Ser. No. 62/772,322, filed Nov. 28, 2018, the contents of which are incorporated by reference herein.

BACKGROUND

Field of the Disclosure

The present disclosure relates to optical detection and determination of a characteristic of a fluid. More particularly, the present disclosure relates to optical dilution or mixing of a fluid in connection with optical detection and determination of a characteristic of the fluid.

Description of Related Art

The color of a fluid may be indicative of a characteristic of the fluid, such as its composition. Thus, when monitoring and/or analyzing a fluid, it may be desirable to detect and measure the color of the fluid. For example, the color of blood or a blood component is indicative of its hematocrit (i.e., its red blood cell content) or free hemoglobin concentration.

Various blood processing systems now make it possible to collect particular blood constituents, instead of whole blood, from a blood source such as, but not limited to, a container of previously collected blood or other living or non-living source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., which is an affiliate of Fresenius Kabi AG of Bad Homburg, Germany, or other centrifugal separation devices, or a spinning membrane-type separator, such as the AUTOPHERESIS-C® and AURORA® devices from Fenwal, Inc.

Systems of this type typically include one or more optical devices for monitoring the composition of the blood or a component thereof. One common approach to non-invasive blood and blood constituent analysis is based on the amount of light transmitted through the fluid. Different blood constituents absorb different wavelengths of light to different degrees, which may be used to determine certain characteristics of a fluid. However, light transmission through fluid containing even low quantities of red blood cells (i.e., fluids having a relatively low hematocrit) may be minimal due to significant scattering of the light. Another possible disadvantage of such transmission-based approaches is that they require access to opposing sides of a fluid path, which may not be available for certain fluid paths in certain systems.

U.S. Pat. No. 9,164,078 (which is hereby incorporated herein by reference) describes a system in which hematocrit of whole blood may be predicted using infrared light. The hematocrit of whole blood is useful information to have for an apheresis system and method because it indicates the red blood cell and plasma quantities available for collection, while the hematocrit of a separated blood component indicates the purity of a component that should contain red blood cells or the contamination of a component that should be free of red blood cells. Furthermore, when mononuclear cells are to be collected, the hematocrit of fluid exiting a separation device may be indicative of the quantity of mononuclear cells exiting the separation device.

The optical devices of these systems may also be configured for measuring the concentration of free hemoglobin of a constituent fluid. For example, U.S. Pat. No. 9,833,557 (which is hereby incorporated herein by reference) describes a system in which the concentration of free hemoglobin in separated plasma may be determined, followed by the determination of an amount of free hemoglobin in a concentrated fluid separated from the plasma. Reliable measurement of free hemoglobin concentration of separated plasma, for example, is useful in determining whether red blood cells are being damaged during separation.

Conventional approaches to free hemoglobin detection involve the measurement of red and green light transmitted through a fluid. While such techniques are capable of producing reliable results, they may be susceptible to disturbances, such as when air bubbles are present in the fluid. When light being transmitted through a fluid encounters air bubbles, the light is scattered, which reduces the amount of light transmitted through the fluid to a light detector and may lead to erroneous measurements. Additionally, plasma or supernatant obtained from a product after separation or during storage is conventionally evaluated using specific free hemoglobin measurement assays, which may be time-consuming and costly. Further, as noted above, it may be impracticable to access opposing sides of a fluid-containing vessel, as required for transmission-based approaches.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of determining a characteristic of a fluid includes providing a vessel including a fluid compartment and a contrast compartment positioned directly adjacent to the fluid compartment. A fluid having a fluid color with a main wavelength is provided in the fluid compartment, while the contrast compartment is configured to have a contrast color with a known main wavelength different from the main wavelength of the fluid color. At least a portion of the vessel is exposed to a light emitted by a broadband light source so as to cause at least a portion of the light to be reflected by the fluid compartment and the contrast compartment. At least a portion of the reflected light is received and analyzed to determine a main wavelength of the received light. A characteristic of the fluid is determined based at least in part on the main wavelength of the received light, the main wavelength of the contrast color, and the percentage of said at least a portion of the vessel occupied by the fluid compartment.

In another aspect, a system is provided for determining a characteristic of a fluid. The system comprises a vessel including a fluid compartment configured to receive a fluid having a fluid color with a main wavelength. The vessel further includes a contrast compartment positioned directly adjacent to the fluid compartment and configured to have a contrast color with a known main wavelength different from the main wavelength of the fluid color. A colorimetric optical sensor device of the system includes a broadband light source configured to emit a light, with at least a portion of the light being exposed to at least a portion of the vessel and reflected by the fluid compartment and the contrast compartment. An optical spectrometer of the colorimetric optical sensor device is configured to receive at least a portion of the reflected light and analyze at least a portion of the received light to determine a main wavelength of the received light. A controller of the colorimetric optical sensor device is configured to determine a characteristic of the fluid based at least in part on the main wavelength of the received light, the main wavelength of the contrast color, and the percentage of said at least a portion of the vessel occupied by the fluid compartment.

In yet another aspect, a vessel is provided for changing the apparent color of a fluid. The vessel includes a fluid compartment configured to receive a fluid having a fluid color with a main wavelength and a contrast compartment positioned directly adjacent to the fluid compartment and configured to have a contrast color with a known main wavelength different from the main wavelength of the fluid color.

These and other aspects of the present subject matter are set forth in the following detailed description of the accompanying drawings.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
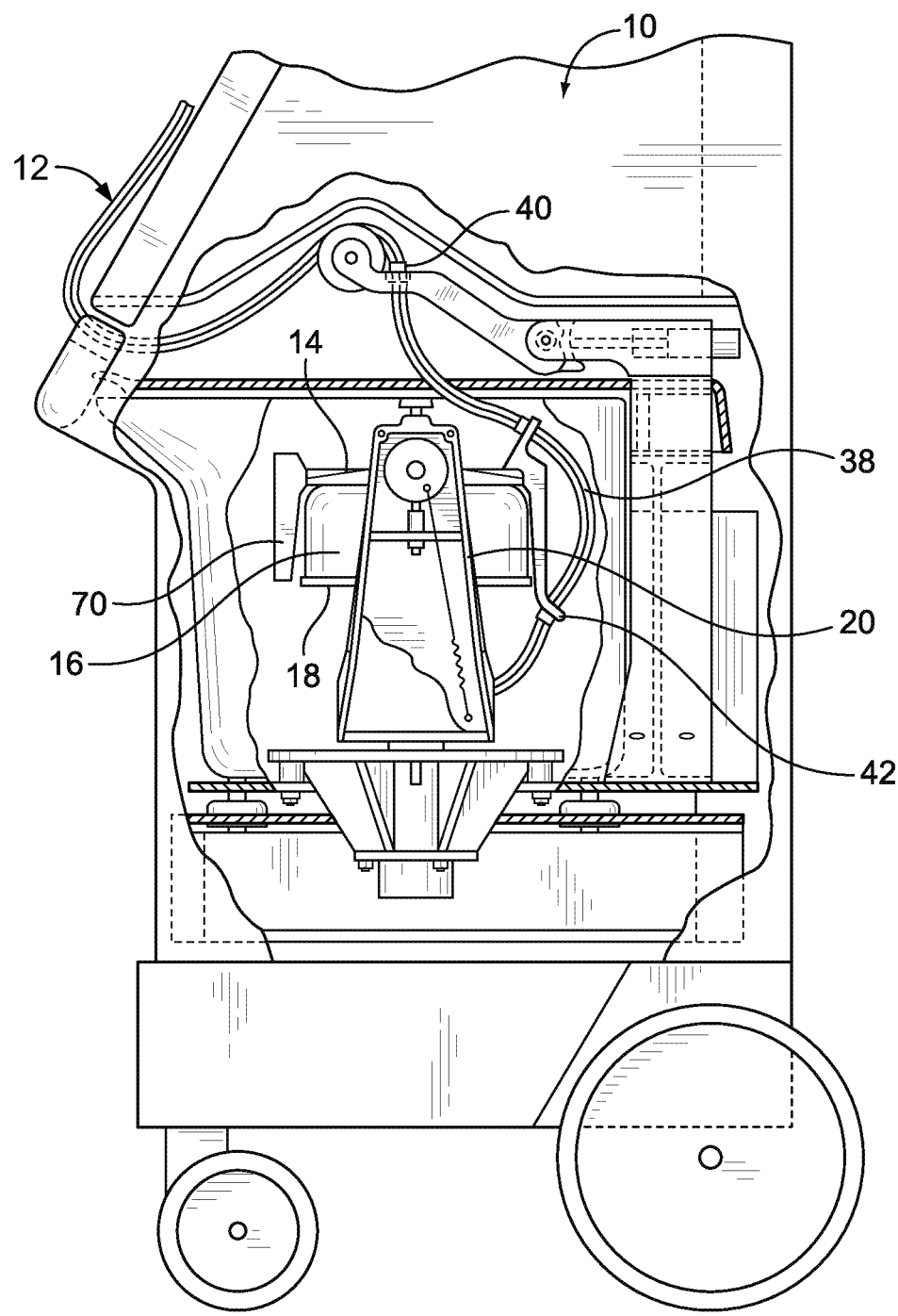
FIG. 1 is a side elevation view, with portions broken away and in section, of a centrifugal fluid separation assembly employing aspects of the present disclosure, with a centrifuge bowl and spool of the assembly being shown in their operating position.
Figure 2:
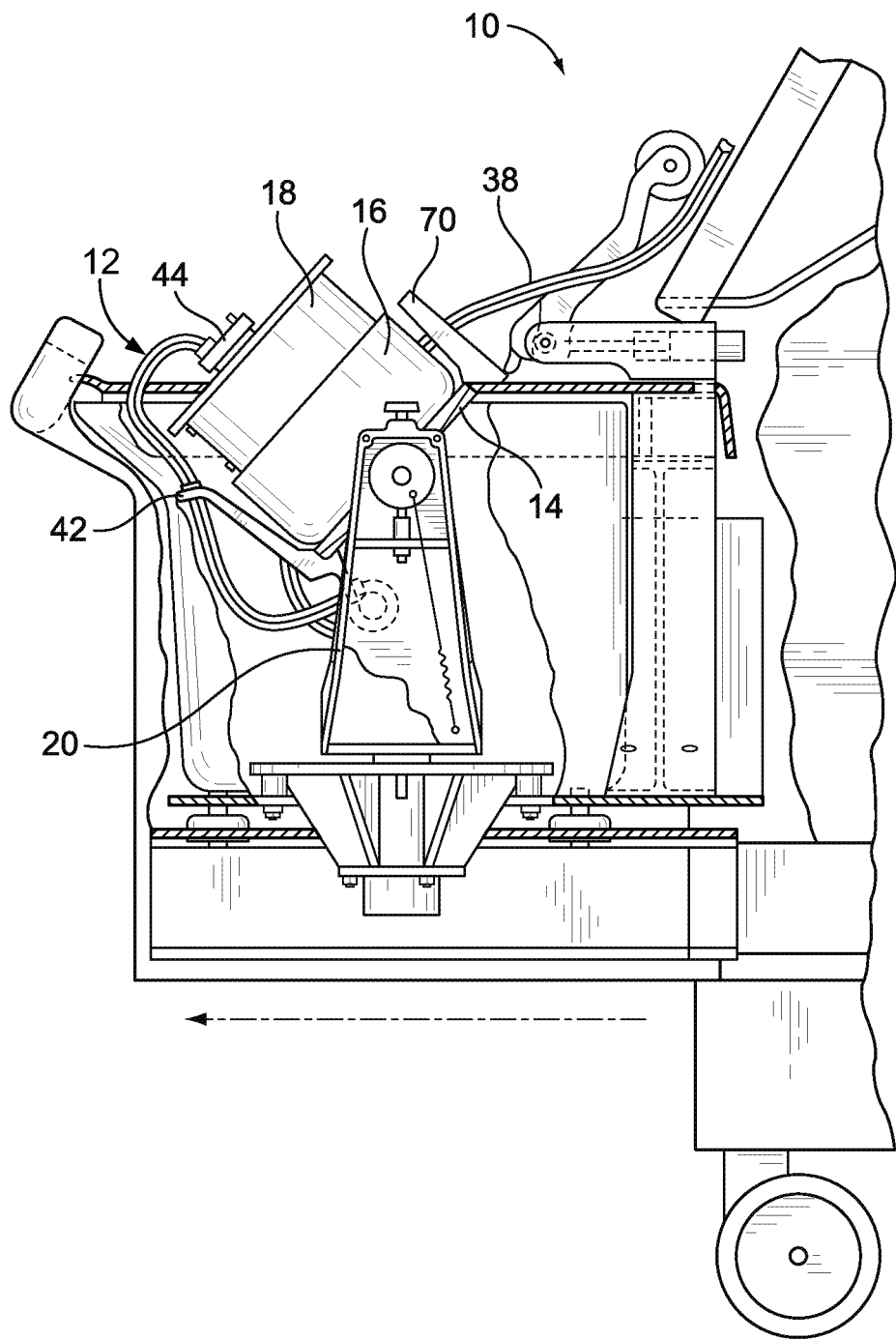
FIG. 2 is a side elevation view, with portions broken away and in section, of the assembly shown in FIG. 1, with the bowl and spool shown in an upright position for receiving a separation chamber.

FIGS. 1 and 2 show a biological fluid processing system that may be used in practicing the optical dilution and color measurement principles of the present disclosure. The system of FIGS. 1 and 2 is currently marketed as the AMICUS® separator of Fenwal, Inc. and is described in greater detail in U.S. Pat. No. 5,868,696, which is hereby incorporated herein by reference. The system can be used for processing various fluids, but is particularly well suited for processing whole blood, blood components, or other suspensions of biological cellular materials. While optical dilution and color measurement principles will be described herein with reference to one particular system, it should be understood that these principles may be employed with other biological fluid processing systems without departing from the scope of the present disclosure. For example, these principles may be practiced with other centrifugal separation systems (including those of the type described in greater detail in U.S. Pat. No. 7,297,272, which is hereby incorporated herein by reference), with "spinning membrane"-type separation systems (including those of the type described in greater detail in U.S. Pat. No. 9,895,482 and PCT Patent Application Publication No. WO 2017/048673 A1, which are hereby incorporated herein by reference), and with biological fluid separation systems based on other separation principles. Additionally, it should be understood that the optical dilution and color measurement principles described herein are not limited to analysis of biological fluids, but are equally applicable to analysis of other fluids, including non-biological fluids.

A. The Centrifuge

The biological fluid processing system comprises a reusable hardware component or separation assembly 10 (FIGS. 1 and 2) and a disposable fluid flow circuit 12 (FIG. 12) that is configured to be mounted to the separation assembly 10 during use. The illustrated separation assembly 10 includes a separation device 14 (illustrated as a centrifuge) used to separate a biological fluid into two or more fluid components or constituents. The separation assembly 10 may be programmed to separate blood or a biological fluid into a variety of components (e.g., platelet-rich plasma and red blood cells), with an exemplary mononuclear cell ("MNC") collection procedure, in which the system separates and collects MNCs (e.g., lymphocytes and monocytes) from whole blood, being described herein. As noted above, it should be understood that centrifugation is only one possible separation technique that may be practiced in combination with the optical dilution and color measurement principles described herein, which principles may also be employed independently of fluid separation.

The illustrated centrifuge 14 is of the type shown in U.S. Pat. No. 5,316,667, which is incorporated herein by reference. The centrifuge 14 comprises a bowl 16 and a spool 18. The bowl 16 and spool 18 are pivoted on a yoke 20 between an operating position (FIG. 1) and a loading/unloading position (FIG. 2).

When in the loading/unloading position, the spool 18 can be opened by movement at least partially out of the bowl 16, as FIG. 2 shows. In this position, the operator wraps a flexible separation chamber 22 (see FIG. 3) of the fluid flow circuit 12 about the spool 18. Closure of the spool 18 and bowl 16 encloses the chamber 22 for processing. When closed, the spool 18 and bowl 16 are pivoted into the operating position of FIG. 1 for rotation about an axis.

B. The Separation Chamber

Figure 4:
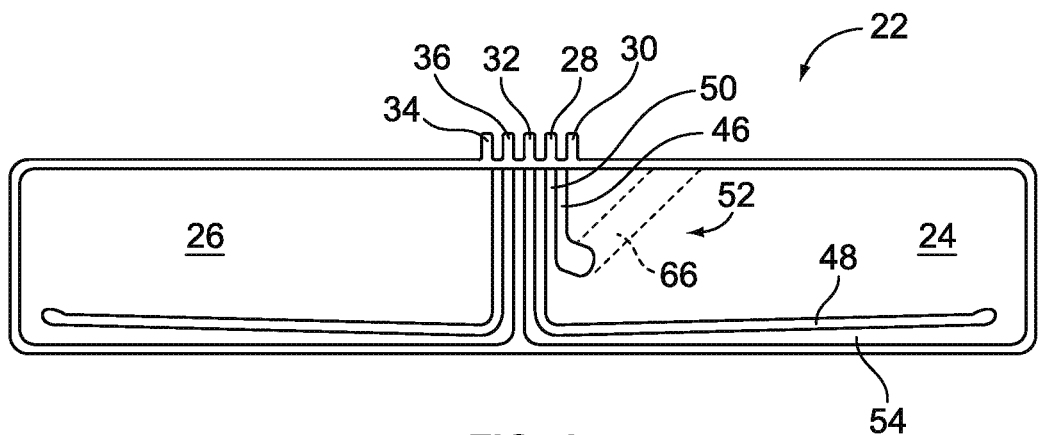
FIG. 4 is a plan view of the separation chamber shown in FIG. 3, out of association with the spool.
Figure 12:
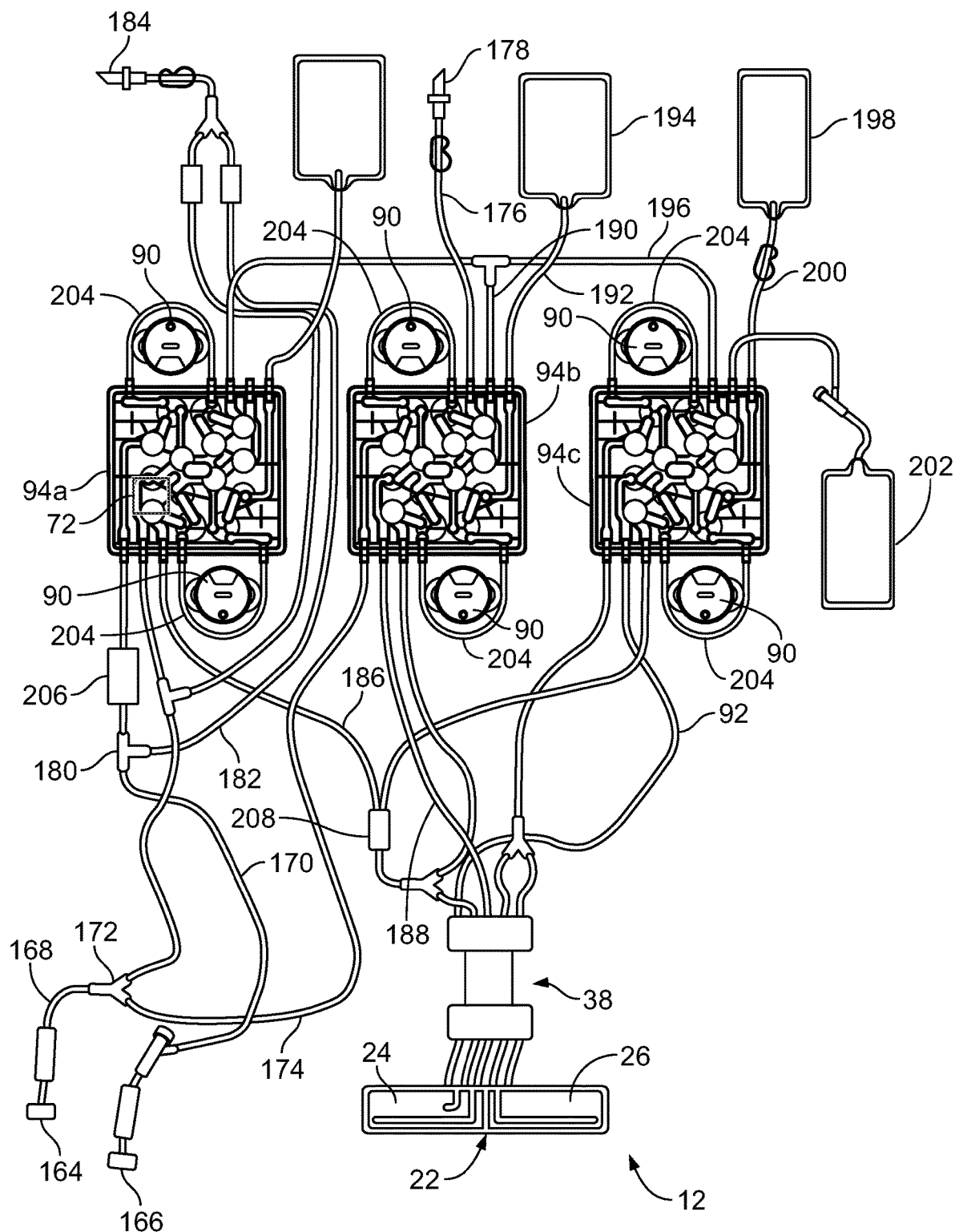
FIG. 12 is a front elevational view of an exemplary disposable fluid flow circuit that may be used in combination with the separation assembly of FIGS. 1 and 2 for carrying out biological fluid separation procedures according to the present disclosure.

The separation chamber 22 can be variously constructed. FIG. 4 shows a representative embodiment, while FIG. 12 shows the separation chamber 22 in the context of a disposable fluid flow circuit 12 that is configured for use in combination with the separation assembly 10 to define a fluid flow path for a biological fluid (e.g., blood), separated fluid components or constituents (e.g., separated blood components), and other fluids (e.g., anticoagulant). It should be understood that the optical dilution and color measurement techniques described herein are not limited to monitoring of any particularly configured extracorporeal biological fluid flow circuit, but may be applied to any fluid flow circuit having an optically appropriate portion or vessel or any other optically appropriate fluid-containing vessel.

The chamber 22 shown in FIG. 4 allows for either single- or multi-stage processing. When used for multi-stage processing, a first stage 24 separates a biological fluid (e.g., whole blood) into first and second components. Depending on the nature of the separation procedure, one of the components may be transferred into a second stage 26 for further separation. When used for single-stage processing, only the first stage 24 is used for separating a biological fluid into its constituents, while the second stage 26 may be filled with saline or the like to balance the chamber 22.

Figure 3:
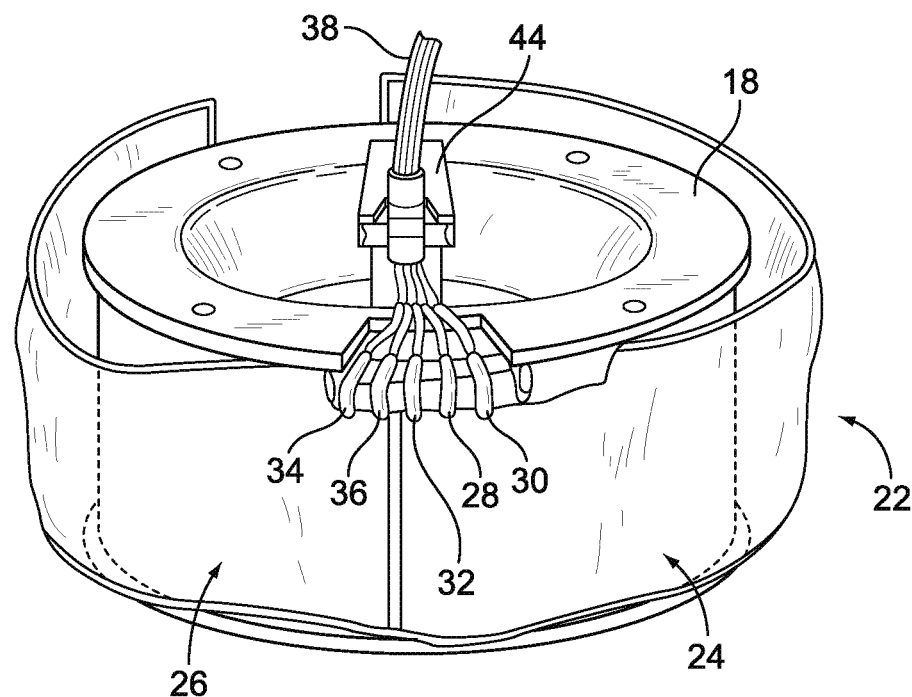
FIG. 3 is a top perspective view of the spool of the centrifuge shown in FIG. 2 in its upright position and carrying the separation chamber.

As FIGS. 3 and 4 best show, there are three ports 28, 30, and 32 associated with the first stage 24. Depending on the particular biological fluid processing procedure, the ports may have different functionality but, in an MNC collection procedure, the port identified at 28 is used for conveying fluids into the first stage 24. During such an MNC collection procedure, the other two ports 30 and 32 serve as outlet ports for separated fluid components exiting the first stage 24. More particularly, the first outlet port 30 conveys a low density fluid component from the first stage 24, while the second outlet port 32 conveys a high density fluid component from the first stage 24.

In a method of carrying out single-stage processing, at least a portion of one or more of the separated components is returned to the fluid source or to some other recipient (either of which may be a living patient or donor or a non-living source, such as a fluid container), while at least a portion of at least one of the other separated components is removed from the first stage 24 and stored. For example, a conventional MNC collection procedure (as described in greater detail in U.S. Pat. No. 5,980,760, which is hereby incorporated herein by reference) begins with a plasma collection phase. During this initial phase, whole blood in the first stage 24 is separated into a plasma constituent (i.e., a low density component, which may include platelets), an interface or buffy coat or MNC-containing layer (i.e., an intermediate density component, which includes MNCs and may also include smaller red blood cells), and packed red blood cells (i.e., a high density component). The plasma constituent and packed red blood cells are removed from the first stage 24 (via the first and second outlet ports 30 and 32, respectively), while the MNC-containing layer builds up in the first stage 24. The plasma constituent is collected, while the packed red blood cells are returned to the blood source.

When a target amount of plasma has been collected, an MNC accumulation phase begins. During this phase, the position of the interface within the first stage 24 is moved closer to the spool 18, such that platelet-rich plasma and packed red blood cells are removed from the first stage 24 (via the first and second outlet ports 30 and 32) while the MNC-containing layer continues to build up in the first stage 24. Portions of the platelet-rich plasma and the packed red blood cells are returned to the blood source, with the remainder of the platelet-rich plasma and packed red blood cells being recirculated through the first stage 24 to maintain a proper hematocrit.

When a target or preselected amount of blood has been processed, the assembly 10 transitions to a red blood cell collection phase. During this phase, blood separation continues as in the MNC accumulation phase, with recirculation and return of the platelet-rich plasma continuing, while the separated red blood cells are conveyed from the first stage 24 and collected for later use rather than being recirculated or returned to the source.

When a target amount of red blood cells has been collected, the assembly 10 transitions to an MNC harvest phase. To harvest the MNCs in the MNC-containing layer, the second outlet port 32 is closed to temporarily prevent packed red blood cells from exiting the first stage 24. At least a portion of the collected red blood cells is conveyed into the first stage 24 via the inlet port 28, which forces the MNC-containing layer to exit the first stage 24 via the first outlet port 30 for collection in an MNC collection container as an MNC product.

Following the MNC harvest phase, a plasma flush phase begins. During this phase, collected plasma is used to flush any MNC-containing layer positioned between the separation chamber 22 and the MNC collection container back into the first stage 24. A portion of the collected plasma may be conveyed into the MNC collection container as a storage or suspension medium for the MNC product.

If additional MNC product is to be collected, the various phases may be repeated. Following collection, the MNC product may be treated to further processing, such as extracorporeal photopheresis.

In a different separation procedure, in which multi-stage processing is required, one of the separated fluid components or constituents will be transferred from the first stage 24 to the second stage 26 via a port 34 associated with the second stage 26. The component transferred to the second stage 26 is further fractionated into sub-components, with one of the sub-components being removed from the second stage 26 via an outlet port 36 and the other sub-component remaining in the second stage 26.

As best shown in FIG. 3, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 2 and 3) rotates the lower end of the umbilicus 38 at a second speed twice the one omega speed (the two omega speed), at which speed the spool 18 and bowl 16 also rotate. This known relative rotation of the umbilicus 38 keeps it untwisted, in this way avoiding the need for rotating seals.

As FIG. 4 shows, a first interior seal 46 is located between the low density outlet port 30 and the inlet port 28. A second interior seal 48 is located between the inlet port 28 and the high density outlet port 32. The interior seals 46 and 48 form a fluid passage 50 (an inlet for whole blood or the like) and a low density collection region 52 in the first stage 24. The second seal 48 also forms a fluid passage 54 (a high density blood component outlet in an MNC collection procedure) in the first stage 24.

Figure 5:
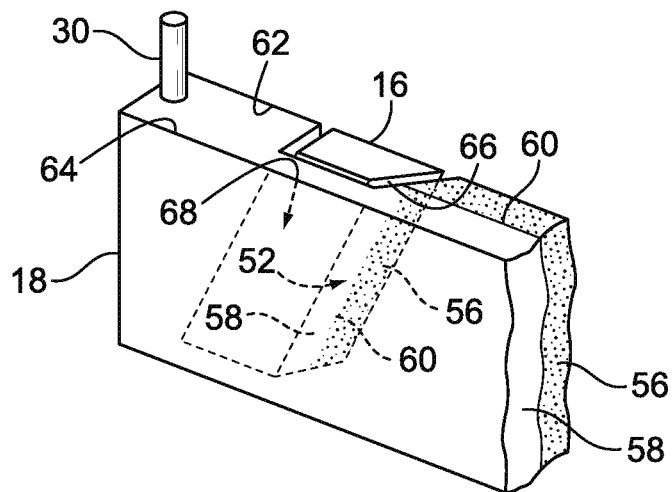
FIG. 5 is an enlarged perspective view of an interface ramp carried by the centrifuge in association with the separation chamber, showing the centrifugally separated red blood cell layer, plasma layer, and interface within the separation chamber when in a desired location on the ramp.

In an MNC collection procedure, the fluid passage 50 channels blood directly into the circumferential flow path immediately next to the low density collection region 52. As shown in FIG. 5, the blood separates into an optically dense layer 56 containing cellular components, which forms as cellular components move under the influence of centrifugal force toward the high-G (outer) wall 62. The optically dense layer 56 will include red blood cells (and, hence, will be referred to herein as the "RBC layer") but, depending on the speed at which the centrifuge 14 is spun, other cellular components (e.g., larger white blood cells and platelets) may also be present in the RBC layer 56.

The movement of the component(s) of the RBC layer 56 displaces less dense blood components radially toward the low-G (inner) wall 64, forming a second, less optically dense layer 58. The less optically dense layer 58 includes plasma (and, hence, will be referred to herein as the "plasma layer or plasma constituent") but, depending on the speed at which the centrifuge 14 is rotated and the length of time that the blood is resident in the centrifuge, other components (e.g., smaller platelets) may also be present in the plasma layer 58.

The transition between the RBC layer 56 and the plasma layer 58 is generally referred to as the interface or buffy coat or MNC-containing layer 60, as described above and shown in FIG. 5. Platelets and white blood cells (including MNCs) typically occupy this transition region.

Figure 6:
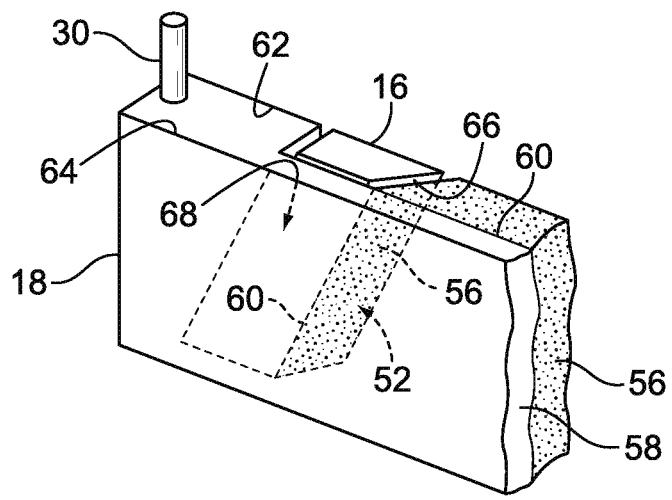
FIG. 6 is an enlarged perspective view of the interface ramp shown in FIG. 5, showing the red blood cell layer and interface at an undesired high location on the ramp.
Figure 7:
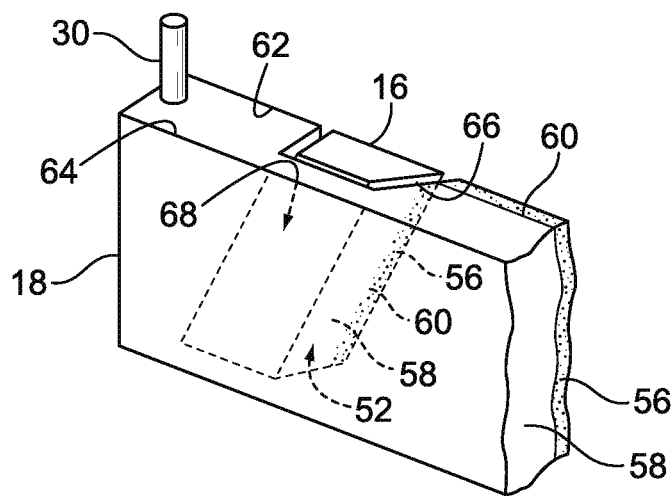
FIG. 7 is an enlarged perspective view of the interface ramp shown in FIG. 5, showing the red blood cell layer and interface at an undesired low location on the ramp.

The location of the interface 60 within the chamber 22 can dynamically shift during blood processing, as FIGS. 6 and 7 show. If the location of the interface 60 is too high (that is, if it is too close to the low-G wall 64 and the removal port 30, as FIG. 6 shows), red blood cells can spill over and into the low density collection region 52, adversely affecting the quality of the plasma constituent 58. On the other hand, if the location of the interface 60 is too low (that is, if it resides too far away from the low-G wall 64, as FIG. 7 shows), the collection efficiency of the assembly 10 may be impaired.

As FIG. 5 shows, a ramp 66 extends from the high-G wall 62 of the bowl 16 at an angle across the low density collection region 52. The angle, measured with respect to the axis of the first outlet port 30 is about 30° in one embodiment. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893, which is incorporated herein by reference.

The ramp 66 forms a tapered wedge that restricts the flow of fluid toward the first outlet port 30. The top edge of the ramp 66 extends to form a constricted passage 68 along the low-G wall 64. The plasma layer 58 must flow through the constricted passage 68 to reach the first outlet port 30.

As FIG. 5 shows, the ramp 66 makes the interface 60 between the RBC layer 56 and the plasma layer 58 more discernible for detection, displaying the RBC layer 56, plasma layer 58, and interface 60 for viewing through the high-G wall 62 of the chamber 22.

Further details of the separation chamber 22 and its operation may be found in U.S. Pat. No. 5,316,667.

C. The Interface Controller

An interface controller (FIG. 11) includes a viewing head or interface optical sensor device 70 carried on the yoke 20 (see FIGS. 1 and 8) and a colorimetric optical sensor device 72, which is shown as being associated with tubing connected to the first outlet port 30 (but which may be variously positioned, as will be described in greater detail herein). Alternatively, rather than being carried on the yoke 20, the interface optical sensor device 70 may be mounted to a radial location of the centrifuge bucket or enclosure, as described in U.S. Patent Application Publication Nos. 2014/0057771 and 2015/0219558, both of which are incorporated herein by reference. The interface optical sensor device 70 is oriented to optically view the transition in optical density between the RBC layer 56 and the plasma layer 58 on the ramp 66. The colorimetric optical sensor device 72 measures the hematocrit and/or free hemoglobin concentration of fluid in an associated portion or vessel of the fluid flow circuit 12 (fluid flowing out of the first stage 24 via the first outlet port 30 in the embodiment of FIG. 11), as will be described in greater detail herein.

The interface controller is functional to determine the location of the interface 60 on the ramp 66 and, if the interface 60 is located at an improper location (e.g., in the locations of FIG. 6 or 7), to correct the location of the interface 60.

(1) The Interface Optical Sensor Device

Figure 8:
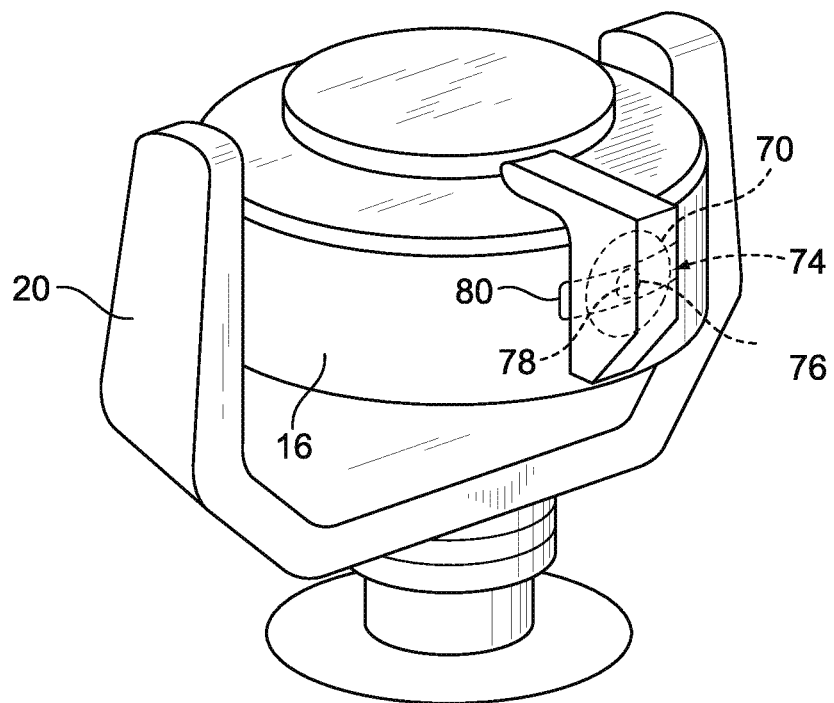
FIG. 8 is a side perspective view of the bowl and spool of the centrifuge when in the operating position, showing a viewing head, which forms a part of an interface controller, being carried by the centrifuge to view the interface ramp during rotation of the bowl.
Figure 9:
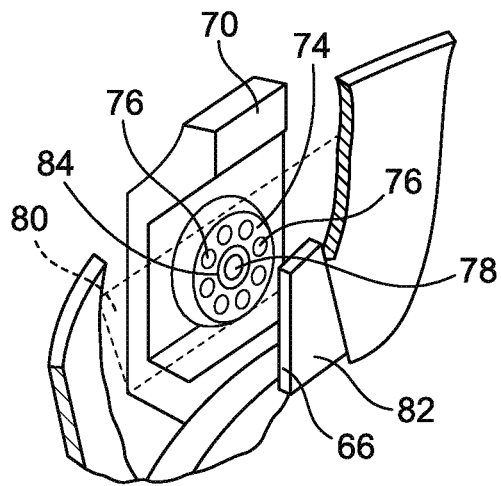
FIG. 9 is a perspective view of the viewing head, with portions broken away and in section, showing the light source and light detector, which are carried by the viewing head, in alignment with the interface ramp, as viewed from within the spool and bowl of the centrifuge.
Figure 10:
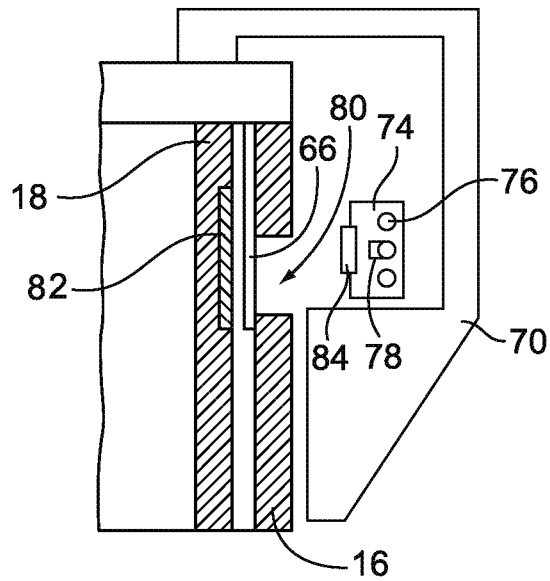
FIG. 10 is a side section view of the bowl, spool, and viewing head when the viewing head is aligned with the interface ramp.

Referring to FIGS. 8-10, the interface optical sensor device 70, carried by the yoke 20 or mounted to a stationary radial location of the centrifuge bucket or enclosure, includes a light source 74, which emits light that is scattered and absorbed by red blood cells. In the illustrated embodiment, the light source 74 includes a circular array of red light emitting diodes 76, but other wavelengths scattered or absorbed by red blood cells, like green or infrared, could also be used.

In the illustrated embodiment, seven light emitting diodes 76 comprise the light source 74. More diodes 76 may be used, or fewer diodes 76 can be used, depending upon the optical characteristics desired. Further, non-LED lights may also be employed without departing from the scope of the present disclosure.

The interface optical sensor device 70 also includes a light detector 78 (FIGS. 9 and 10), which is mounted adjacent to the light source 74. In one embodiment, the light detector 78 comprises a PIN diode detector, which is located generally in the geometric center of the circular array of light emitting diodes 76. Other types of light detectors may also be employed.

If mounted to the yoke 20, the yoke 20 and the interface optical sensor device 70 rotate at a one omega speed, as the spool 18 and bowl 16 rotate at an average speed of two omega. If mounted to a stationary portion of the centrifuge bucket or enclosure, the interface optical sensor device 70 remains stationary while the yoke 20 rotates at a one omega speed and the spool 18 and bowl 16 rotate at an average speed of two omega. The light source 74 directs light onto the rotating bowl 16. In the illustrated embodiment, the bowl 16 is transparent to the light emitted by the source 74 only in the region 80 where the bowl 16 overlies the interface ramp 66 (FIG. 8). In the illustrated embodiment, the region 80 comprises a window cut out in the bowl 16. The remainder of the bowl 16 that lies in the path of the interface optical sensor device 70 comprises an opaque or light absorbing material.

The interface ramp 66 is made of a light transmissive material. The light from the source 74 will thereby pass through the transparent region 80 of the bowl 16 and the ramp 66 every time the rotating bowl 16 and interface optical sensor device 70 align. The spool 18 may also carry a light reflective material 82 (FIGS. 9 and 10) behind the interface ramp 66 to enhance its reflective properties. The spool 18 reflects incoming light received from the source 74 out through the transparent region 80 of the bowl 16, where it is sensed by the detector 78. In the illustrated embodiment, light passing outward from the source 74 and inward toward the detector 78 passes through a focusing lens 84 (shown in FIGS. 9 and 10), which forms a part of the viewing head 70.

Such an arrangement optically differentiates the reflective properties of the interface ramp 66 from the remainder of the bowl 16. This objective can be achieved in other ways. For example, the light source 74 could be gated on and off with the arrival and passage of the ramp 66 relative to its line of sight. As another example, the bowl 16 outside the transparent region 80 could carry a material that reflects light, but at a different intensity than the reflective material 82 behind the interface ramp 66.

As the transparent interface region 80 of the bowl 16 comes into alignment with the interface optical sensor device 70, the detector 78 will first sense light reflected through the plasma layer 58 on the ramp 66. Eventually, the RBC layer 56 adjacent the interface 60 on the ramp 66 will enter the optical path of the interface optical sensor device 70. The RBC layer 56 scatters and absorbs light from the source 74 and thereby reduces the previously sensed intensity of the reflected light. The length of time that the higher intensity of reflected light is sensed by the detector 78 represents the amount of light from the source 74 that is not scattered or absorbed by the RBC layer 56 adjacent to the interface 60. With this information, a processing element or module 86 (FIG. 11) can determine the location of the interface 60 on the ramp 66 relative to the constricted passage 68. A more detailed discussion of the algorithms by which the interface controller receives and processes signals to determine the location of the interface 60 on the ramp 66 may be found in U.S. Pat. No. 6,312,607, which is incorporated herein by reference.

Figure 11:
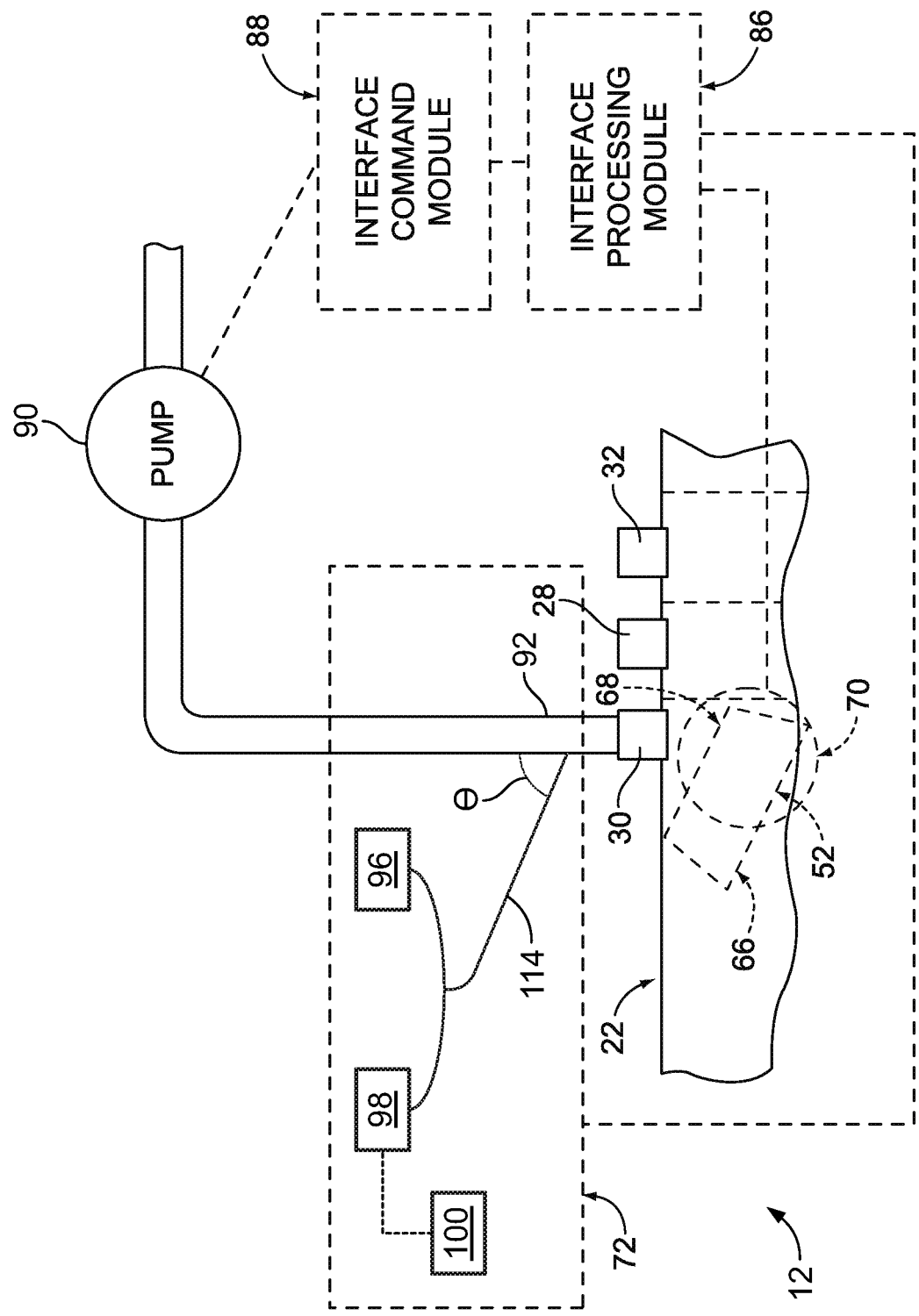
FIG. 11 is a schematic view of components of the interface controller including a colorimetric optical sensor device.

When the location of the interface 60 on the ramp 66 has been determined, the processing element 86 outputs that information to an interface command element or module 88 (FIG. 11). The command element 88 includes a comparator, which compares the interface location output with a desired interface location to generate an error signal. The error signal may take a number of forms but, in one embodiment, is expressed in terms of a targeted red blood cell percentage value (i.e., the percentage of the ramp 66 which should be occupied by the RBC layer 56).

When the control value is expressed in terms of a targeted red blood cell percentage value, a positive error signal indicates that the RBC layer 56 on the ramp 66 is too small (as FIG. 7 shows). The interface command element 88 generates a signal to adjust an operational parameter accordingly, such as by increasing the rate at which plasma is removed through the first outlet port 30 under action of a pump 90 (FIG. 11). The interface 60 moves toward the constricted passage 68 to the desired control position (as FIG. 5 shows), where the error signal is zero.

A negative error signal indicates that the RBC layer 56 on the ramp 66 is too large (as FIG. 6 shows). The interface command element 88 generates a signal to adjust an operational parameter accordingly, such as by decreasing the rate at which plasma is removed through the first outlet port 30. The interface 60 moves away from the constricted passage 68 to the desired control position (FIG. 5), where the error signal is again zero.

(2) The Colorimetric Optical Sensor Device

The interface controller may further include a colorimetric optical sensor device 72, which is shown in FIG. 11 as being configured to monitor the fluid exiting the first stage 24 of the separation chamber 22 via the first outlet port 30. The fluid exiting the first stage 24 via the first outlet port 30 is typically platelet-poor plasma or platelet-rich plasma, but depends on the procedure being executed by the system. For example, the MNC-containing layer will and the RBC layer may exit the first outlet port 30 during the MNC harvest phase of an MNC collection procedure of the type described herein.

While the colorimetric optical sensor device 72 is shown in FIG. 11 as monitoring a tube 92 connected to the first outlet port 30, it should be understood that the colorimetric optical sensor device 72 may be located and configured to monitor fluid in any optically appropriate portion or vessel of the fluid flow circuit 12. This may include vessels in which fluid is in motion (e.g., flowing through a tube or through the separation chamber 22) and vessels in which fluid is substantially stationary (e.g., a collection or storage bag or container or a cuvette or test tube), as well as vessels positioned either upstream or downstream of the separation chamber 22. For example, FIG. 12 shows the colorimetric optical sensor device 72 monitoring fluid in a cassette 94*a* of the fluid flow circuit 12, which fluid may be anticoagulated whole blood flowing through or stationary within the cassette 94*a*. Furthermore, while the illustrated colorimetric optical sensor device 72 is shown as being incorporated into the interface controller, it is also within the scope of the present disclosure for the colorimetric optical sensor device 72 to be separately provided and either work cooperatively with the interface controller or entirely independently.

The colorimetric optical sensor device 72 detects the color of the fluid in the associated vessel of the fluid flow circuit 12 to assess the hematocrit and/or free hemoglobin concentration of the fluid. If platelet-poor plasma or some other cell-free supernatant is present in the vessel and the color of the fluid is more red than it should be, then it may be indicative of conditions of hemolysis or contamination by red blood cells. The colorimetric optical sensor device 72 may also detect a change in the nature of a fluid, such as when the fluid exiting the first outlet port 30 transitions from the MNC-containing layer to the RBC layer during the MNC harvest phase of an MNC collection procedure. The information obtained and output by the colorimetric optical sensor device 72 may be used to modify the separation procedure, such as by changing the speed at which a pump 90 operates or causing the transition from one phase of a separation procedure to another phase. For example, if the output is indicative of the presence of red blood cells in a subject fluid that is intended to be substantially free of red blood cells, the output may be used modify the separation procedure in a way that reduces contamination of the fluid by red blood cells (e.g., by moving the position of the interface 60 within the separation chamber 22). If the output is indicative of an elevated free hemoglobin concentration, the output may be used to modify the separation procedure in a way that reduces the incidence of hemolysis (e.g., by reducing the rate at which the separation device is rotated).

The colorimetric optical sensor device 72 includes a broadband light source 96, an optical spectrometer 98, and a controller 100. The broadband light source 96 is configured to emit a light including at least all wavelengths in the visible range (from approximately 400 nm to approximately 700 nm), but may also include wavelengths above and/or below the visible range. In one embodiment, the broadband light source 96 is provided as a stabilized tungsten-halogen light source (configured to emit a light having all wavelengths between 360 nm and 2600 nm) of the type marketed by Thorlabs, Inc. of Newton, N.J., but the broadband light source 96 may also be differently configured without departing from the scope of the present disclosure.

Figure 13:
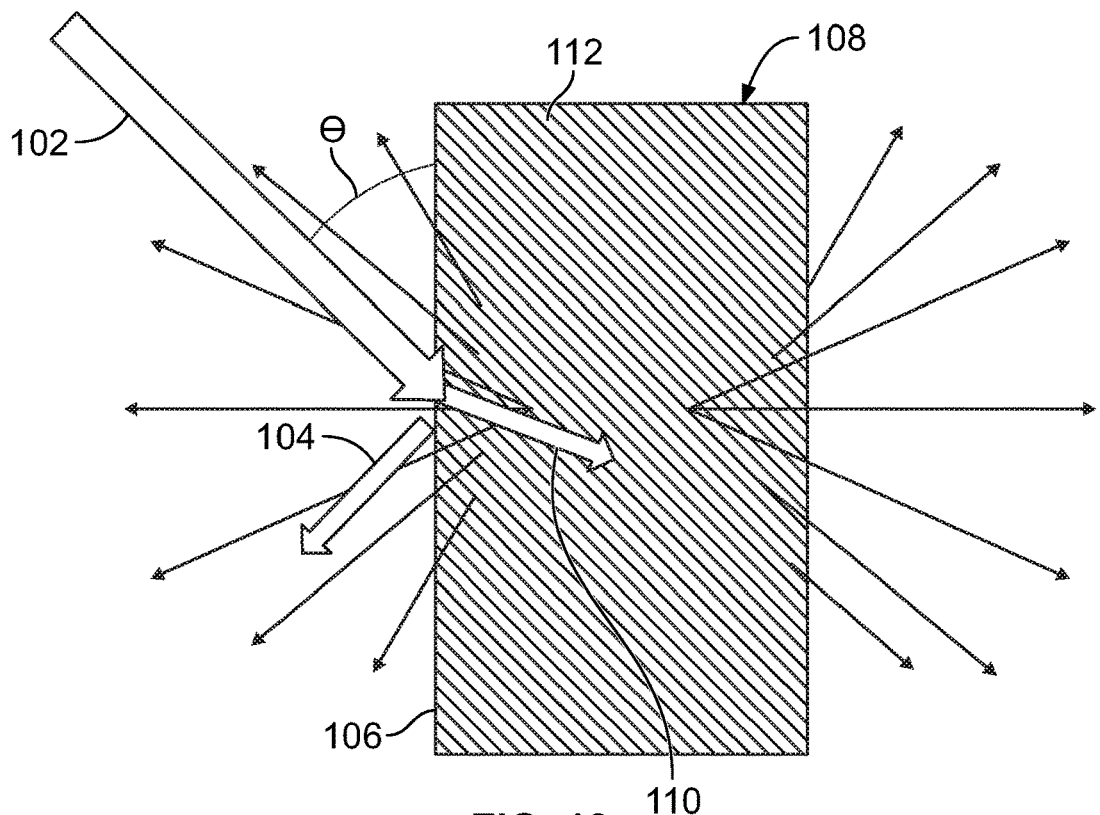
FIG. 13 is a schematic view of light from a broadband light source of the colorimetric optical sensor device of FIG. 11 entering into a fluid-containing vessel.

The broadband light source 96 is oriented to emit light toward a vessel of the fluid flow circuit 12 (the tube 92 in FIG. 11 or the cassette 94*a* in FIG. 12) in which fluid is present. FIG. 13 shows the light 102 emitted by the broadband light source 96, with a first portion 104 of the light 102 reflecting off of a surface 106 of the vessel 108 (specular reflection), while a second portion 110 of the light 102 is transmitted through the surface 106 and into the vessel 108. As shown in FIGS. 11 and 13, the light 102 may be directed to strike the surface 106 of the vessel 108 at an angle $\Theta$, which may be selected to reduce the degree of specular reflection. For example, if the angle $\Theta$ is 90°, there will tend to be a significant amount of specular reflection. On the other hand, if the angle $\Theta$ is 0° (i.e., if the light 102 is parallel to the surface 106), then the fluid 112 in the vessel 108 will not be exposed to any light. It has been found that an angle in the range of 30-60° (which may be approximately 45°, in one embodiment) may be advantageous for reducing the degree of specular reflection and producing more sensitive color measurements.

Figure 14:
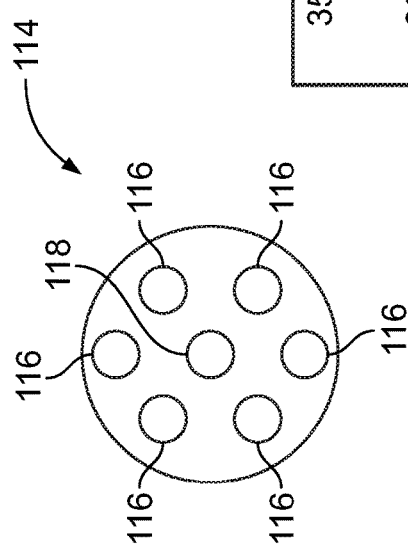
FIG. 14 is a cross-sectional view of an optical bundle of the colorimetric optical sensor device of FIG. 11.

The broadband light source 96 itself may be oriented to direct the light 102 at a particular angle $\Theta$ with respect to the surface 106 of the vessel 108. Alternatively, at least one transmitting optical fiber may be provided to direct at least a portion of the light 102 from the broadband light source 96 to the surface 106 of the vessel 108 at a particular angle $\Theta$. FIG. 11 shows an optical fiber bundle 114, which includes a plurality of optical fibers. In one embodiment, the optical fiber bundle 114 is provided as a fiber bundle reflection probe of the type marketed by Thorlabs, Inc., having optical fibers with a 200 µm diameter. A cross-sectional view of the optical fiber bundle 114 is shown in FIG. 14, which shows seven optical fibers, with six outer optical fibers 116 and one inner optical fiber 118 positioned centrally with respect to the other optical fibers 116. In the illustrated embodiment, the outer optical fibers 116 comprise transmitting optical fibers configured to transmit light from the broadband light source 96 to the surface 106 of the vessel 108, while the central or inner optical fiber 118 comprises a receiving optical fiber configured to transmit reflected light to the optical spectrometer 98. It should be understood that the illustrated configuration of the optical fiber bundle 114 is merely exemplary and that other configurations may also be employed if an optical fiber bundle is provided. For example, in other embodiments, there may be only a single transmitting optical fiber, a plurality of receiving optical fibers, and/or optical fibers differently arranged than as shown in FIG. 14.

Figure 15:
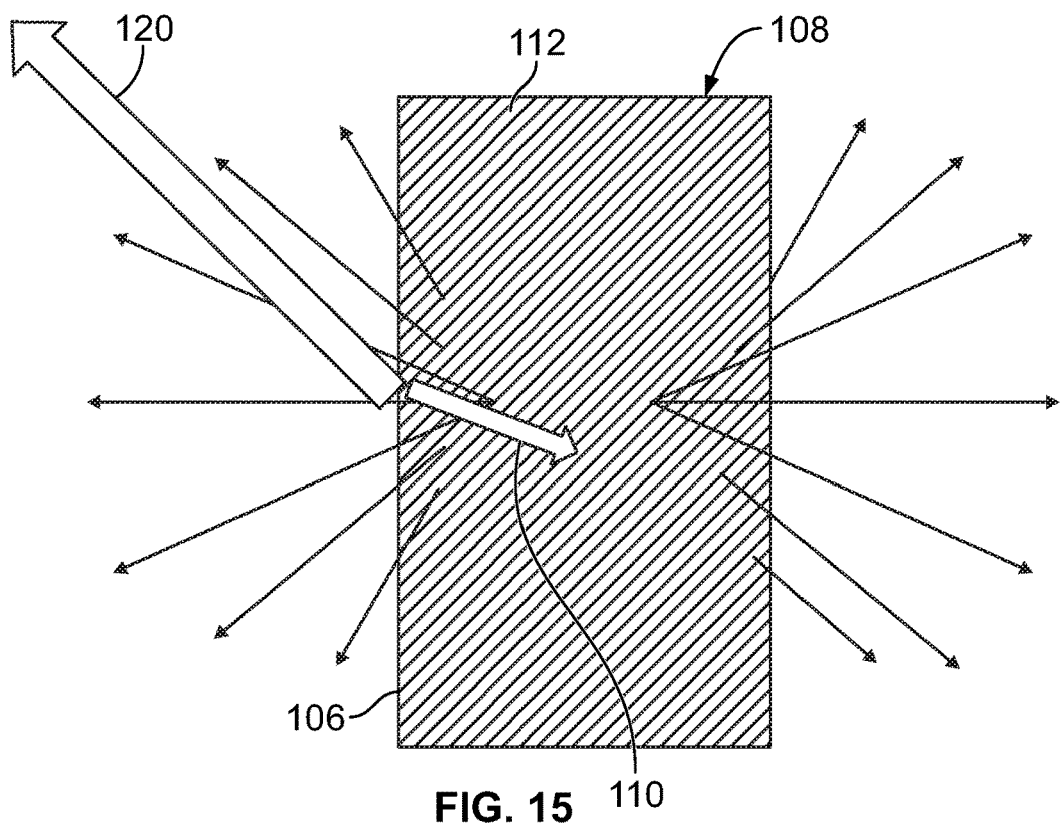
FIG. 15 is a schematic view of light reflecting off of the fluid in the vessel of FIG. 13 for receipt and analysis by the colorimetric optical sensor device of FIG. 11.

The light 102 strikes the surface 106 of the vessel 108 and the portion 110 not reflected is transmitted through the surface 106 and into the vessel 108 at an angle according to Snell's Law. The portion 110 of light that enters the fluid 112 is absorbed and scattered based on the unique optical properties of the fluid 112, with a portion 120 of the transmitted light 110 being reflected back out of the vessel 108 (FIG. 15) for receipt by the optical spectrometer 98. If a receiving optical fiber 118 is provided, at least a portion of the reflected light 120 is directed to the optical spectrometer 98 by the receiving optical fiber 118.

The optical spectrometer 98 is configured for measurement and wavelength differentiation of at least a portion of the reflected light that it receives. In one embodiment, the optical spectrometer 98 is provided as a compact CCD spectrometer capable of measuring the intensity of light at each wavelength in the range of 200 nm-1000 nm of the type marketed by Thorlabs, Inc., but it may also be differently configured without departing from the scope of the present disclosure.

Figure 16:
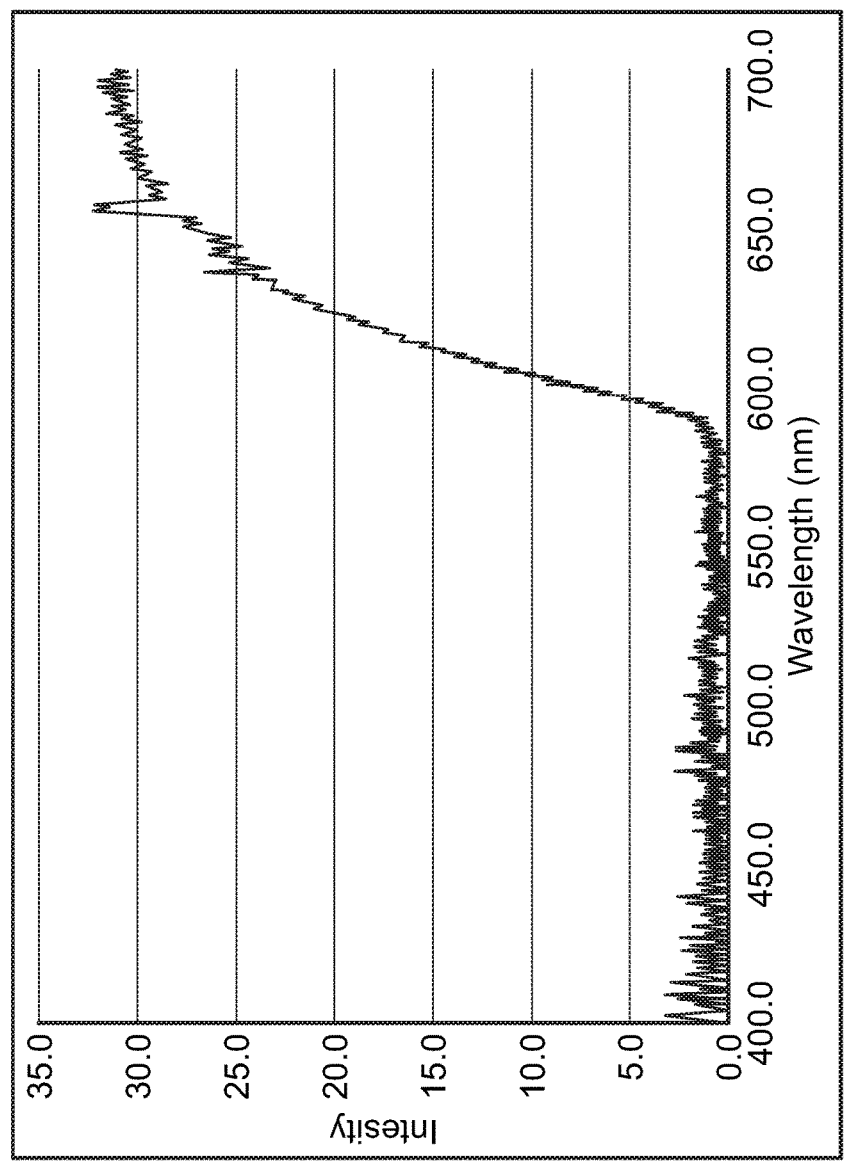
FIG. 16 is a chart illustrating an exemplary optical spectrum produced by a colorimetric optical sensor device in measuring the hematocrit of a fluid.
Figure 17:
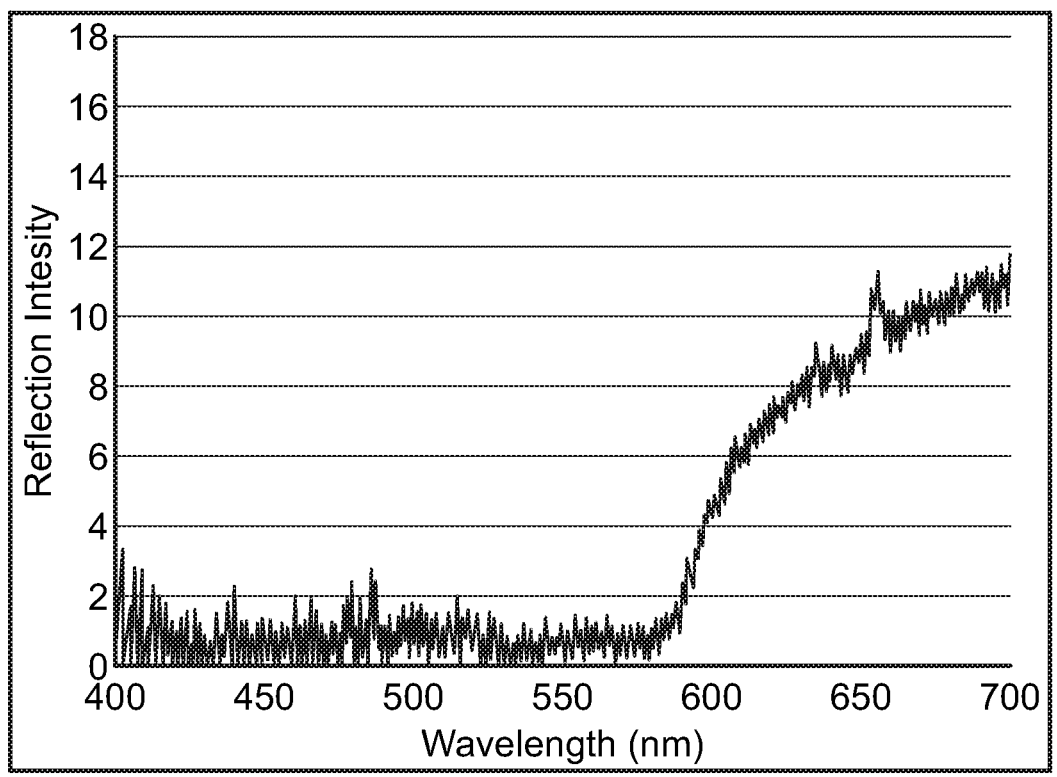
FIG. 17 is a chart illustrating an exemplary optical spectrum produced by a colorimetric optical sensor device in measuring the free hemoglobin concentration of a fluid.

The optical spectrometer 98 analyzes at least a portion of the received light and differentiates the wavelengths contained within the light to produce an optical spectrum of the light, as shown in FIGS. 16 and 17. FIGS. 16 and 17 show the intensity of the light at different wavelengths for a fluid having a hematocrit of 8.5% and for a fluid having a free hemoglobin concentration of 400 mg/dL, respectively. In each case, the greatest intensities are displayed for wavelengths above 600 nm, indicating that the fluids are some shade of red in color. The main wavelength is then determined from the optical spectrum, such as by using a conventional color specification system, which may be software of the type marketed by Thorlabs, Inc.

The controller 100 then correlates the main wavelength to a corresponding hematocrit or free hemoglobin concentration. The controller 100 may be variously configured without departing from the scope of the present disclosure. In one embodiment, the controller 100 may include a microprocessor (which, in fact may include multiple physical and/or virtual processors). According to other embodiments, the controller 100 may include one or more electrical circuits designed to carry out the actions described herein. In fact, the controller 100 may include a microprocessor and other circuits or circuitry. In addition, the controller 100 may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessor to carry out one or more actions as described below.

Figure 18:
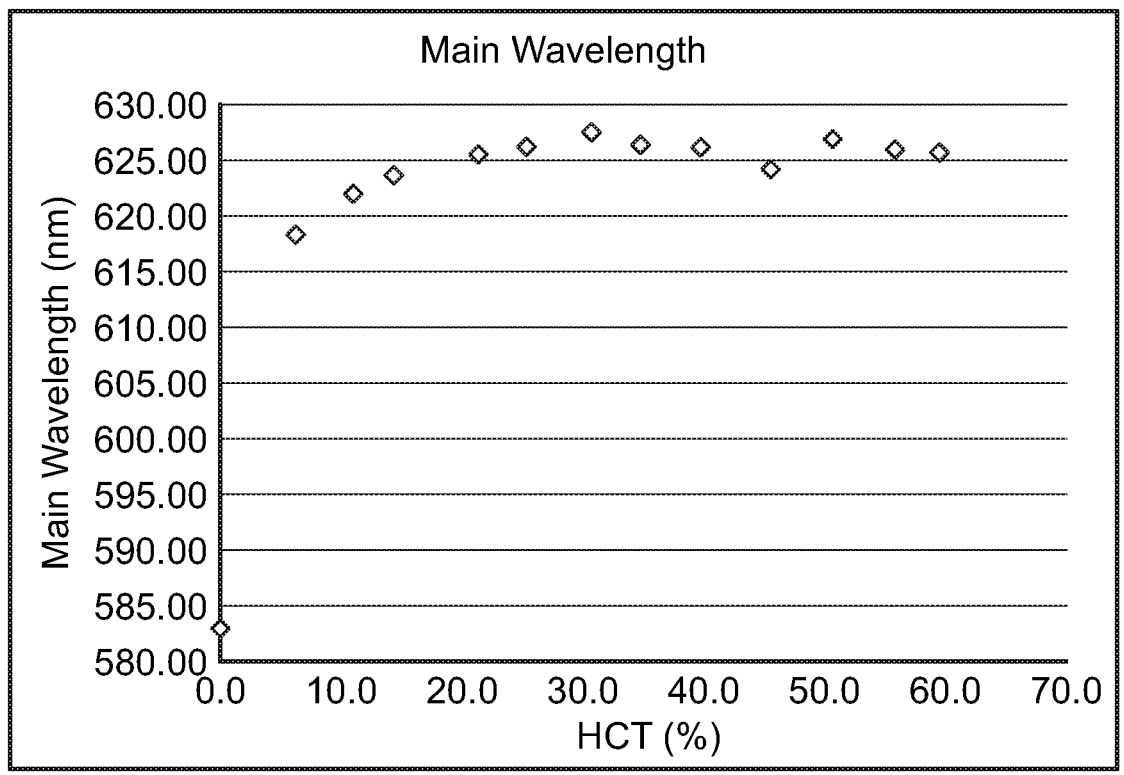
FIGS. 18 and 19 are charts illustrating a relationship between the main wavelength of a broadband light reflected by a fluid and the hematocrit of that fluid.
Figure 19:
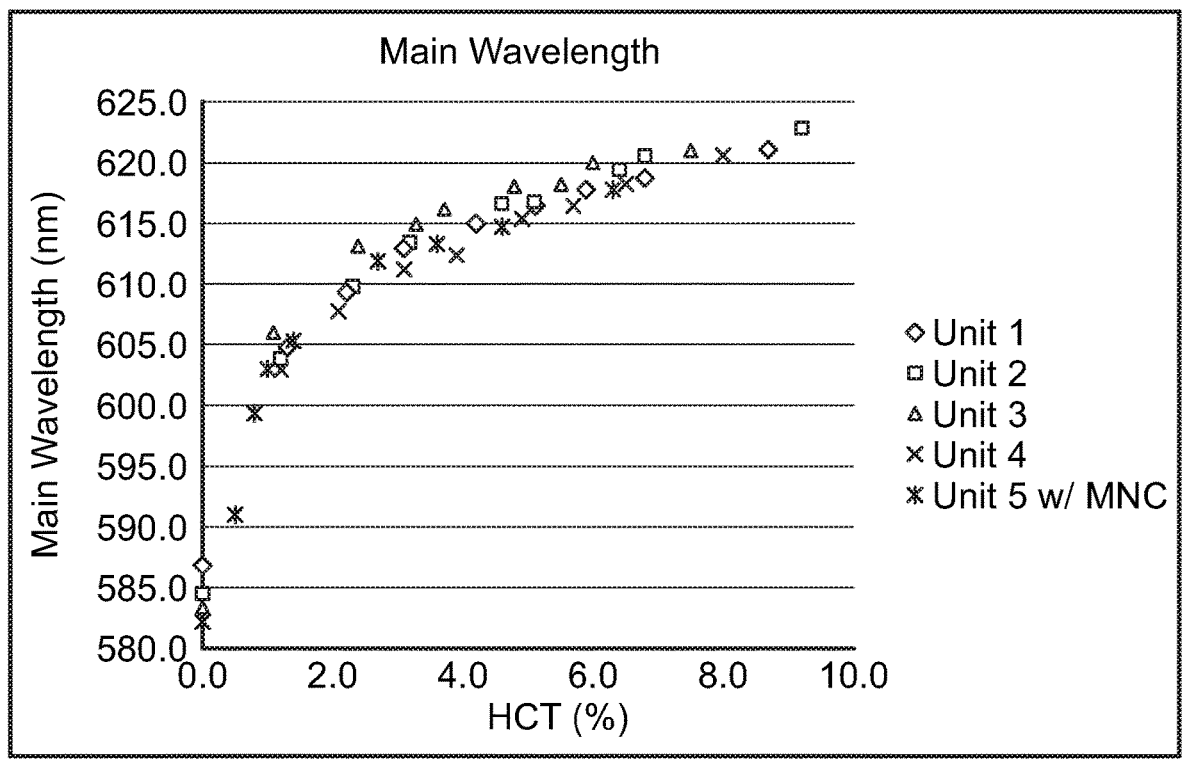
Figure 20:
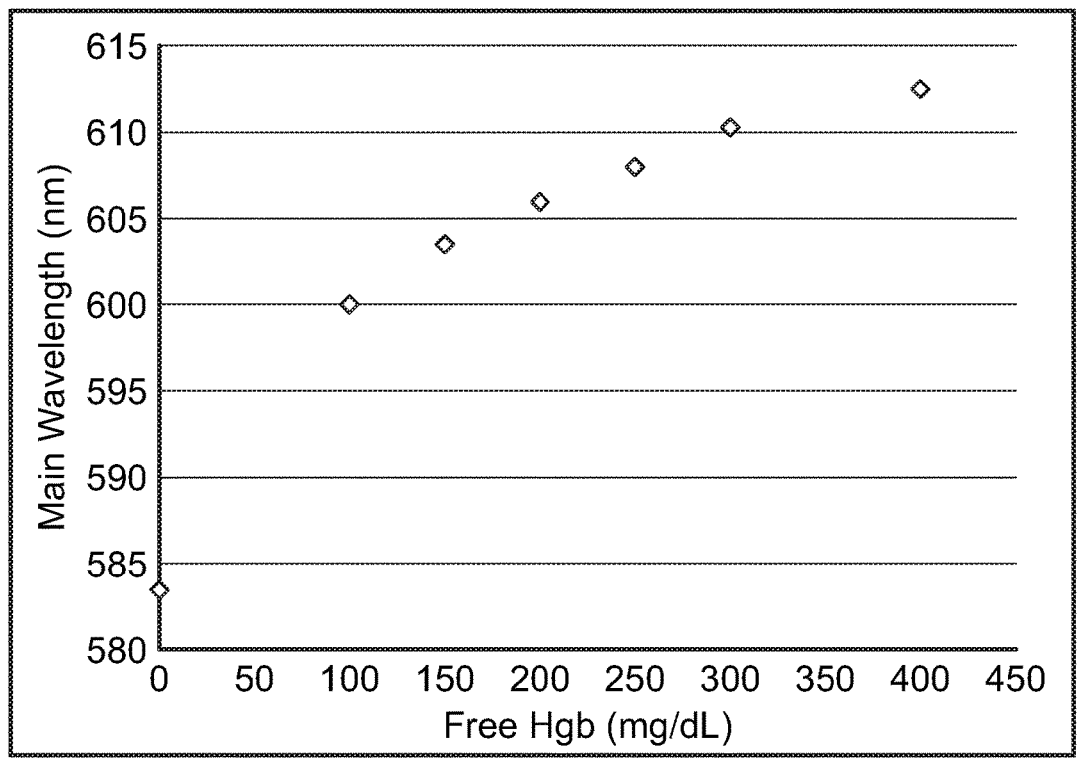
FIG. 20 is a chart illustrating a relationship between the main wavelength of a broadband light reflected by a fluid and the free hemoglobin concentration of that fluid.

FIG. 18 shows an experimentally determined correlation between main wavelength and hematocrit in a range between 0% and 60%, while FIG. 19 more particularly shows an experimentally determined correlation between main wavelength and hematocrit in a range between 0% and 9.5%. FIG. 20 shows an experimentally determined correlation between main wavelength and free hemoglobin concentration in a range between 0 mg/dL and 400 mg/dL. The correlations shown in FIGS. 18-20 may be generated by determining the main wavelength of a fluid having a known hematocrit (in the case of FIGS. 18 and 19) or a known free hemoglobin concentration (in the case of FIG. 20). As confirmed by FIGS. 18-20, a greater hematocrit or a higher free hemoglobin concentration results in fluid having a darker shade of red (i.e., a higher main wavelength within the visible range). The main wavelength is, thus, determined by the particular hematocrit or free hemoglobin concentration of the subject fluid, meaning that knowledge of the main wavelength of a fluid in a vessel allows for determination of the hematocrit or free hemoglobin concentration of that fluid.

FIG. 19 shows the results of testing carried out using samples derived from five different blood sources to evaluate the repeatability of the method and the impact that variation in red blood cell characteristics (e.g., mean corpuscular volume and mean corpuscular hemoglobin concentration) may have on the variation of the measurement. The results show promising repeatability from person-to-person, while also showing that a sample containing high concentrations of white blood cells (the fifth sample) does not alter the color measurement technique. FIG. 19, thus, confirms the correlation between main wavelength and hematocrit.

Whether the redness of the subject fluid is due to the presence of red blood cells or free hemoglobin may be determined by the most likely cause of redness in view of a number of factors, which may include the nature of the fluid, the location of the portion or vessel being monitored with respect to the separation device, and the nature of the separation device. For example, when monitoring the plasma or supernatant outlet line of a "spinning membrane"-type separator (such as one of the type described in U.S. Pat. No. 9,895,482 and PCT Patent Application Publication No. WO 2017/048673 A1), it is expected that the fluid will be free of cellular blood components (including red blood cells), such that any redness of the fluid will be understood to be on account of free hemoglobin. Conversely, when monitoring the low density outlet of a centrifuge (e.g., the tube 92, as in FIG. 11), the incidence of contamination by red blood cells is more common than hemolysis, such that any redness of the fluid will be understood to be on account of the presence of red blood cells. Alternatively, an approach of the type described in U.S. patent application Ser. No. 16/429,128, which is hereby incorporated herein by reference, in which the color of the fluid at different times is compared, may be employed to differentiate between redness caused by the presence of red blood cells and redness caused on account of free hemoglobin.

When the controller 100 has correlated the main wavelength to a corresponding hematocrit or free hemoglobin concentration, it may generate an output that is indicative of that value. The output of the controller 100 may be directed to the interface command module 88 or some other module of the interface controller to control separation of the biological fluid or may be put to some other use.

The foregoing approach to measuring fluid color and determining hematocrit and/or free hemoglobin concentration has several advantages. For example, as can be seen in FIG. 11, the broadband light source 96 and the optical spectrometer 98 (i.e., the light detector) are positioned on the same side of the vessel, rather than requiring access to opposing sides of the vessel, which makes it more readily used in combination with any portion or vessel of a fluid flow circuit 12 (or any other fluid-containing vessel). Additionally, this approach is not sensitive to the presence of air bubbles in the fluid. Furthermore, if the hematocrit of the MNC-containing layer exiting the separation chamber 22 is known (by using the colorimetric optical sensor device 72 to monitor an appropriate vessel, as in the embodiment of FIG. 11), it is more practicable to replace the above-described batch collection of MNCs with a continuous collection approach because collection efficiency and MNC product purity may be improved by continuous monitoring and procedure modification (e.g., changing the rate of operation of a pump 90 in response to an output from the controller 100).

As can be seen in FIG. 18, the correlation between main wavelength and hematocrit may be greater between 0% and 20% than above 20%. Accordingly, if a fluid having an elevated hematocrit (e.g., whole blood, which may have a hematocrit on the order of approximately 38-55%) is to be analyzed, it may be advantageous for the fluid in the vessel to comprise a diluted fluid in order to lighten the color of the fluid to a level having a clearer correlation between main wavelength and hematocrit (i.e., preferably to a level below 20% or, more preferably, to a level below 10%).

According to one approach to dilution of a fluid, a fluid of interest is diluted with another fluid (e.g., saline) to reduce the redness of the fluid of interest. The main wavelength and hematocrit of the diluted fluid are determined, as described above. Then, the hematocrit of the fluid of interest (i.e., the fluid in its undiluted or less diluted state) may be determined, followed by the controller 100 generating an alternative or additional output that is indicative of the hematocrit of the fluid of interest. For example, to use this approach to measure the hematocrit of whole blood (having an unknown hematocrit, which is 45% in this example), a 2:1 dilution (two parts solution, such as saline, to one part whole blood) may be used to dilute the blood by a factor of three to bring the (unknown) hematocrit to a level that is within the 0-20% range (15% in this example). The controller 100 would determine the hematocrit of the diluted fluid to be 15% (based on the main wavelength of the diluted fluid), followed by the controller 100 multiplying the determined hematocrit by three (due to the known dilution factor of three) to arrive at the 45% value of the whole blood (i.e., the fluid of interest). While this approach is described with respect to a fluid having a relatively high hematocrit, it should be understood that it is equally applicable to a fluid having a relatively high free hemoglobin concentration or with any other fluid that is better analyzed by the applicable colorimetric optical sensor device at a different level of color (which may be darker or lighter than the color of the fluid).

Alternatively, rather than diluting the fluid of interest with another fluid, it may be preferable to instead optically dilute or optically mix the fluid (i.e., change its apparent color without changing the nature of the fluid). According to such an approach, the fluid of interest and another distinctly colored substance are placed into close proximity to give the appearance of a third color (different from the color of the fluid of interest and the other substance) when perceived from an appropriate distance by the optical spectrometer 96, without changing the compositions or colors of the fluid of interest and the other substance.

Figure 21:
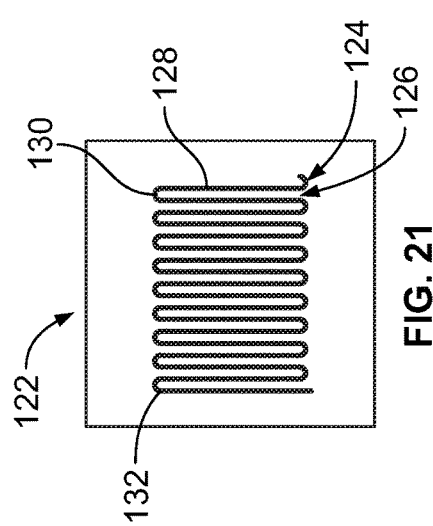
FIG. 21 is a top plan view of an exemplary embodiment of a vessel configured for optical mixing of a fluid.

FIG. 21 shows an exemplary vessel 122 that is suitable for optically diluting or mixing a fluid. The vessel 122 includes a fluid compartment 124 and a contrast compartment 126 positioned directly adjacent to the fluid compartment 124. The fluid compartment 124 is configured to be filled with the fluid to be analyzed (e.g., whole blood), which has a fluid color having a main wavelength, as described above. The vessel 122 may be incorporated into or otherwise in fluid communication with a fluid flow circuit (such as the one illustrated in FIG. 12), in which case fluid may be pumped or otherwise conveyed into the fluid compartment 124 as part of a procedure involving the fluid. Alternatively, the vessel 122 may be separate from a fluid flow circuit, with the fluid being injected or conveyed into the fluid compartment 124 by any suitable means. For example, blood may be introduced into the fluid compartment 124 via a finger prick approach.

As for the contrast compartment 126, it is configured to have a contrast color with a known main wavelength that is different from the main wavelength of the fluid in the fluid compartment 124. While the main wavelength of the color of the fluid in the fluid compartment 124 is not known, it may be estimated (e.g., if it is known that the vessel 122 will be used to analyze whole blood), with an appropriate contrast color being selected in view of the estimated main wavelength of the color of the fluid in the fluid compartment 124. For example, if anticoagulated whole blood is to be analyzed, it may be advantageous for the contrast color to be yellow or clear, which results in a clear distinction between the main wavelengths of the fluid color and the contrast color and lowers the main wavelength of the light received and analyzed by the optical spectrometer 98 of an associated colorimetric optical sensor device 72, as will be described in greater detail herein. While this is an example of selecting a contrast color with a main wavelength that is less than the main wavelength of the color of the fluid being analyzed, it is also within the scope of the present disclosure to select a contrast color with a main wavelength that is greater than the main wavelength of the fluid color, which increases the main wavelength of the light received and analyzed by an optical spectrometer 98.

The contrast color may be achieved by any of a number of suitable approaches. For example, the material forming the contrast compartment 126 may be manufactured to present the contrast color. Alternatively, the contrast compartment 126 may be hollow and configured to receive a contrast fluid or material which presents (or combines with the material forming the contrast compartment 126 to present) the contrast color. For example, if the contrast color is to be yellow, the contrast compartment 126 may be formed of a yellow material (e.g., a yellow plastic material) or may be formed of a clear, translucent material and be configured to receive a contrast fluid or material having a yellow color.

The fluid compartment 124 and the contrast compartment 126 may be variously configured without departing from the scope of the present disclosure. For example, in the embodiment of FIG. 21, the fluid compartment 124 is defined by a plurality of elongated and substantially parallel rows 128, with each row 128 being fluidly connected to an adjacent row 128 by a 180° curved section 130. Adjacent rows 128 of the fluid compartment 124 are spaced apart by an elongated row 132 of the contrast compartment 126, which rows 132 of the contrast compartment 126 may be substantially parallel. In the illustrated embodiment, the length of the rows 128 and 132 is significantly greater (e.g., on the order of ten times greater or more) than the width or thickness of the rows 128 and 132. If the contrast compartment 126 is configured to receive a contrast fluid, then it may be advantageous for the various rows 132 of the contrast compartment 126 to be fluid connected to allow them all to be filled with the contrast fluid.

Figure 22:
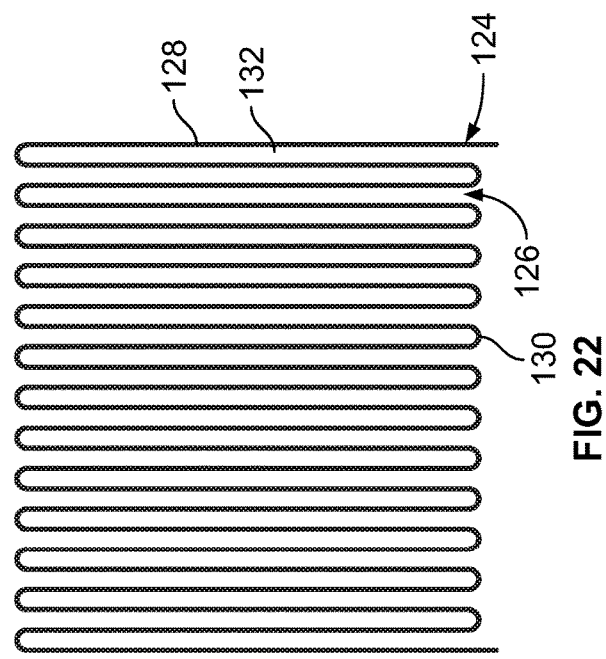
FIG. 22 is a top plan view of an alternative embodiment of a vessel configured for optical mixing of a fluid.

In the embodiment of FIG. 21, the rows 128 of the fluid compartment 124 have a uniform or constant width or thickness, which is the same width or thickness as the rows 132 of the contrast compartment 126. In other embodiments, the width or thickness of the rows 128 of the fluid compartment 124 may be different from the width or thickness of the rows 132 of the contrast compartment 126. For example, FIG. 22 shows an embodiment in which the rows 128 of the fluid compartment 124 have a different width or thickness from the rows 132 of the contrast compartment 126, with the rows 132 of the contrast compartment 126 being wider or thicker than the rows 128 of the fluid compartment 124. While FIG. 22 shows an embodiment in which the rows 132 of the contrast compartment 126 are wider or thicker than the rows 128 of the fluid compartment 124, it is also within the scope of the present disclosure for the rows 128 of the fluid compartment 124 to be wider or thicker than the rows 132 of the contrast compartment 126.

Figure 23:
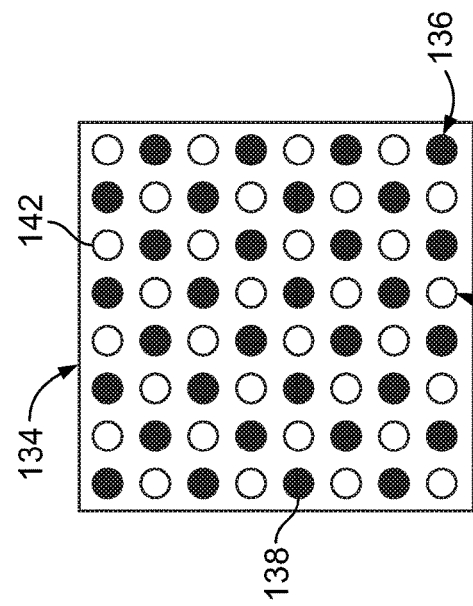
FIG. 23 is a top plan view of another alternative embodiment of a vessel configured for optical mixing of a fluid.

FIG. 23 shows an alternative vessel configuration. In the vessel 134 of FIG. 23, the fluid compartment 136 is comprised of a plurality of isolated regions 138 (shown in FIG. 23 as shaded circles), with the contrast compartment 140 being comprised of a plurality of isolated regions 142 (shown in FIG. 23 as unshaded circles) alternating with the isolated regions 138 of the fluid compartment 136. It should be understood that the vessel 134 of FIG. 23 is enlarged to better illustrate its configuration, as it is advantageous for the isolated regions 138 and 142 to be relatively small (e.g., each having a diameter on the order of approximately 100-500 μm). The various isolated regions 138 of the fluid compartment 136 may be separate from each other or may be fluidly connected on the underside of the vessel 134 to allow for them all to be filled with the subject fluid. The isolated regions 138 and 142 are shown as being circular, substantially identical, and arranged in a "checkered" pattern. In variations to the configuration of FIG. 23, the isolated regions 138 and 142 may be non-circular (e.g., square), differently configured (e.g., with the isolated regions 142 of the contrast compartment 140 being larger and/or differently shaped than the isolated regions 138 of the fluid compartment 136), and/or arranged in a different pattern. While different patterns are possible, it may be advantageous for the pattern to be uniform, such that the isolated regions 138 and 142 provide the appearance of a uniform color when viewed from an appropriate distance.

Figure 24:
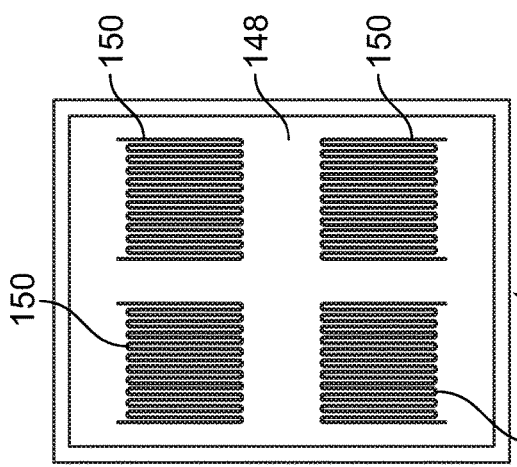
FIG. 24 is a top plan view of a first mold for forming a first portion of an optical mixing vessel.
Figure 25:
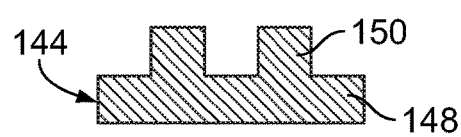
FIG. 25 is a cross-sectional view of a portion of the first mold of FIG. 24.
Figure 26:
FIG. 26 is a cross-sectional view of a portion of a second mold for forming a second portion of an optical mixing vessel.

As the vessel may be variously configured, it may be variously formed. In one example, the vessel is configured as a microfluidic chip, as in FIG. 21, with the fluid compartment (and optionally the contrast compartment) configured as a microfluidic channel having a width or thickness on the order of approximately 100-500 μm. In such an embodiment, fluid may be flowed into the fluid compartment of the microfluidic chip (e.g., via a finger prick to analyze blood), followed by the microfluidic chip being inserted into a fixture for analyzation by a colorimetric optical sensor device 72 mounted to or otherwise associated with the fixture. FIGS. 24 and 25 show an exemplary mold 144 for forming a first portion of a vessel configured as a microfluidic chip, while FIG. 26 shows a portion of an exemplary second mold 146 for forming a second portion of such a vessel. FIGS. 27-31 illustrate a method of using the molds 144 and 146 to form the vessel.

Figure 28:
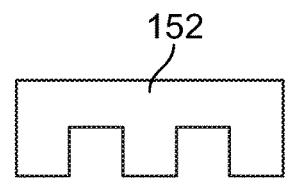
FIGS. 27-31 illustrate steps in an exemplary method of manufacturing an optical mixing vessel.

The first mold 144 has a flat, horizontal base 148, with an upwardly extending pattern or projection 150 (FIGS. 24 and 25) that corresponds to the microfluidic channel of the vessel to be formed. The mold 144 of FIG. 24 includes a plurality of patterns 150, thus allowing for the channels of a plurality of vessels to be formed simultaneously. In use, a mold material is poured into the first mold 144 and allowed to cure, as in FIG. 27. In one embodiment, the mold material is a 10:1 (by weight) mixture of a pre-polymer (which may be a silicone material, such as SYLGARD® 184 PDMS of Dow Corning Corporation of Midland, Mich.) and a curing agent. Once the mold material has cured, it is removed from the mold 144, leaving a first portion 152 of a vessel (FIG. 28). The imprint left in the mold material by the pattern 150 will define the channel or fluid compartment of the vessel.

Figure 29:
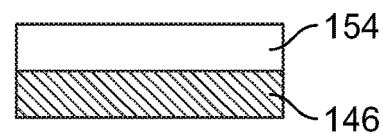
Figure 27:
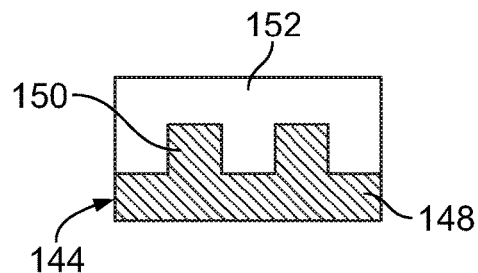
Figure 30:
Figure 31:
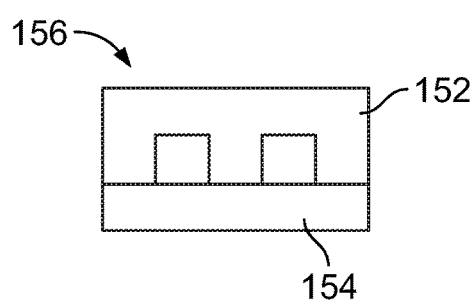

The second mold 146 is flat (FIG. 26), such that a mold material poured into the second mold 146 (which may be the same mold material poured into the first mold 144 or a different mold material) will settle into a flat layer (FIG. 29). The flat layer of mold material is allowed to partially cure, such that it hardens into a mostly solid second portion 154 of a vessel (FIG. 30) without becoming fully solid.

The fully cured first portion 152 the vessel is then placed onto the partially cured second portion 154 (FIG. 31), with the voids defined in the first portion 152 by the pattern 150 facing the second portion 154. The second portion 154 is then allowed to fully cure, thus causing the first and second portions 152 and 154 to fully bond together, forming the vessel 156, with the voids defining the fluid compartment. It should be understood that this is merely one suitable approach for forming a vessel configured as a microfluidic chip and that other approaches may be employed without departing from the scope of the present disclosure.

Figure 32:
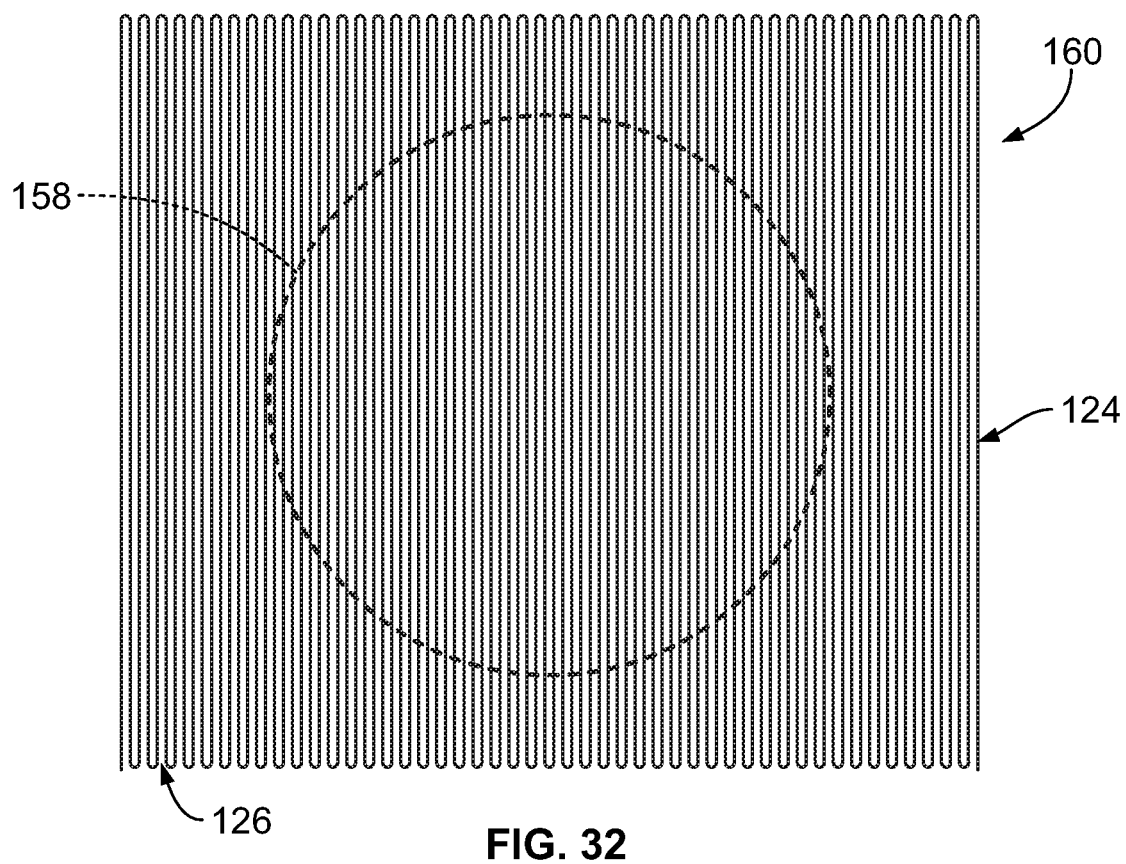
FIG. 32 is a top plan view of an alternative embodiment of a vessel configured for optical mixing of a fluid.

Regardless of the particular configuration of the fluid and contrast compartments and the manner in which they are formed, they are preferably configured so as to give the appearance of a third, uniform color when viewed from an appropriate distance. The colorimetric optical sensor device 72 perceives this third color by illuminating all or a portion of the vessel with light 102 from its light source 96. FIG. 32 shows an illuminated portion 158 of a vessel 160, which is struck by light 102 from the light source 96. The color perceived by the optical spectrometer 98 of the colorimetric optical sensor device 72 will be a composite of the fluid color and the contrast color, with the main wavelength of the light received by the optical spectrometer 98 being somewhere between the main wavelength of the fluid color and the main wavelength of the contrast color. If the fluid compartment 124 and the contrast compartment 126 occupy equal percentages of the illuminated portion 158 of the vessel 160, then it may be expected for the main wavelength of the received light to be the average of the main wavelengths of the fluid color and the contrast color. On the other hand, if the fluid compartment 124 occupies some other percentage of the illuminated portion 158 of the vessel 160, then the main wavelength of the received light may be closer to the main wavelength of the fluid color (if the fluid compartment 124 occupies more than 50% of the illuminated portion 158 of the vessel 160) or closer to the main wavelength of the contrast color (if the fluid compartment 124 occupies less than 50% of the illuminated portion 158 of the vessel 160).

The percentage of the illuminated portion 158 of the vessel 160 occupied by the fluid compartment 124 may thus be understood as being equivalent to the dilution ratio when physically (rather than optically) diluting a subject fluid. For example, selecting a vessel in which the fluid compartment occupies half of the illuminated portion of the vessel (as in FIGS. 21, 23, and 32-33) may be understood as being equivalent to physical dilution of the subject fluid at a 1:1 ratio. Similarly, a 2:1 optical dilution of a subject fluid may be achieved by selecting a vessel in which the fluid compartment occupies half as much of the illuminated portion of the vessel as the contrast compartment (as in FIG. 22, in which the rows 132 of the contrast compartment 126 are twice as thick or wide as the rows 128 of the fluid compartment 124). Thus, to use this approach to measure the hematocrit of whole blood (having an unknown hematocrit, which is 45% in this example), a 2:1 optical dilution (in which the fluid compartment occupies one-third of the illuminated portion of the vessel and the contrast compartment occupies two-thirds of the illuminated portion) may be used to optically mix or dilute the blood by a factor of three to bring the (unknown) hematocrit to a level that is within the 0-20% range (15% in this example, assuming a contrast color with a main wavelength approaching 0 nm).

Upon determining the main wavelength of the received light, the controller 100 of the colorimetric optical sensor device 72 may determine the main wavelength of the subject fluid, as described above with respect to physical dilution of a subject fluid. The controller 100 may then make further use of such information, such as using the main wavelength of a biological fluid to determine its hematocrit or free hemoglobin concentration.

Figure 33:
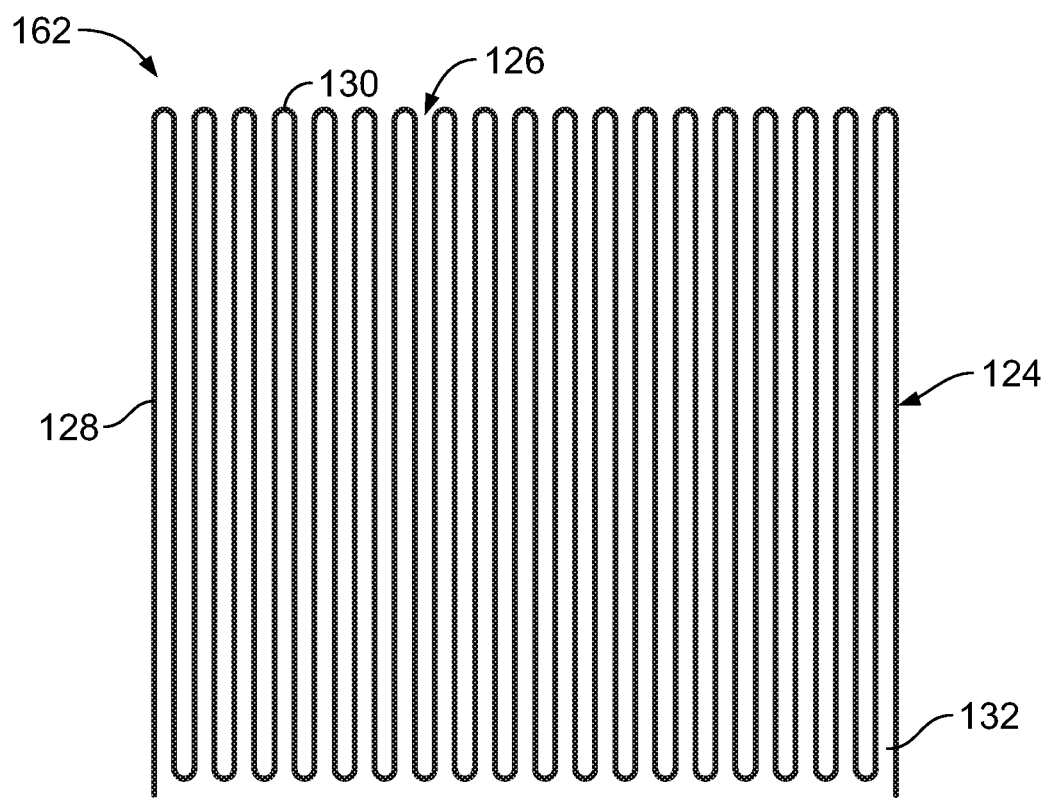
FIG. 33 is a top plan view of another alternative embodiment of a vessel configured for optical mixing of a fluid.

As described above, the vessel must be viewed by the colorimetric optical sensor device 72 from an appropriate distance so as to perceive a uniform, composite color. The distance from which the vessel is most preferably viewed (e.g., by a colorimetric optical sensor device 72) may vary depending on the configuration of the vessel and the associated colorimetric optical sensor device 72. In general, the farther the viewer is from the vessel, the greater the vessel gives the appearance of a third, uniform color. For example, FIGS. 32 and 33 illustrate similarly configured vessels 160 and 162 (which are configured according to the preceding description of the embodiment of FIG. 21, with the fluid compartment 124 and the contrast compartment 126 having equally sized rows) viewed from different distances. When viewed from a greater distance (compare FIG. 32 to FIG. 33), the different colors of the fluid compartment 124 and the contrast compartment 126 are more difficult to individually perceive, instead optically mixing together to give the appearance of a third or composite color that is different from the fluid color and the contrast color. The configuration of the vessel may also affect the optimal viewing distance, with thinner rows (in the embodiments of FIGS. 21-22 and 32-33) or smaller, more closely positioned isolated regions (in the embodiment of FIG. 23) giving the appearance of a more uniform third or composite color from a smaller minimum viewing distance than when thicker rows or larger isolated regions are employed. Additionally, the larger the portion of the vessel illuminated by the colorimetric optical sensor device 72 (i.e., the larger the various fibers 116, 118 of the optical fiber bundle 114 in the illustrated embodiment), the smaller the minimum viewing distance may be.

According to one approach to determining the optimal viewing distance for a particular vessel and a particular colorimetric optical sensor device, a control vessel may be provided. The control vessel may be comparably sized and configured to the subject vessel, but omit the contrast compartment. The control vessel is filled with a sample fluid and analyzed (e.g., using the methods described herein) to determine its main wavelength. The subject vessel (with the subject fluid contained within the fluid compartment) is then analyzed using a colorimetric optical sensor device positioned a selected distance from the subject vessel. The main wavelength of the color perceived by the colorimetric optical sensor device is determined (as described above), followed by the colorimetric optical sensor device determining the main wavelength of the sample fluid. If the main wavelength of the sample fluid determined by the colorimetric optical sensor device is incorrect, then the distance between the vessel and the colorimetric optical sensor device may be changed (such as by being increased), followed by the main wavelength of the sample fluid being determined at the new distance. This process may be repeated until the colorimetric optical sensor device has determined the correct main wavelength of the sample fluid, with the distance between the vessel and the colorimetric optical sensor device being considered to be appropriate for the optical mixing principles described herein.

In one particular example, in which the vessel is configured as a microfluidic channel having a width or thickness on the order of approximately 100-500 μm, it may be advantageous for an associated colorimetric optical sensor device 72 to view the vessel from a distance in the range of approximately 0.5 inch to approximately 1.0 inch for improved optical mixing (i.e., the appearance of a more uniform third or composite color, as opposed to the constituent fluid and contrast colors being perceptible) compared to a lesser distance. In other embodiments, it may be acceptable for the viewing distance to be greater or less than the range of 0.5 inch to 1.0 inch. However, it may be advantageous for the minimum viewing distance to be on the order of 1.0 inch or less or at least no more than a few inches to allow for a more compact system. As for the maximum distance from which the vessel is advantageously viewed by an associated colorimetric optical sensor device 72, it may depend on the configuration of the colorimetric optical sensor device 72 (e.g., the maximum viewing distance may be limited by the strength of the light source 96). Thus, it should be understood that the optimal viewing distance or range of viewing distances may vary without departing from the scope of the present disclosure.

D. Fluid Flow Circuit

FIG. 12 shows an exemplary fluid flow circuit 12 that may be used in carrying out the hematocrit and/or free hemoglobin concentration measurement techniques described herein. The illustrated fluid flow circuit 12 has a "two needle" configuration, which includes a pair of fluid source access devices 164 and 166 (e.g., phlebotomy needles) configured for direct connection to a fluid source. The fluid source access devices 164 and 166 are connected by tubing 168 and 170 (referred to herein as a draw line and a return line, respectively) to a first or left cassette 94a. One of the fluid source access devices 164 is used to draw fluid (e.g., blood in an MNC collection procedure) from the fluid source into the fluid flow circuit 12 and is connected to the left cassette 94a through a y-connector 172. The other leg of the y-connector 172 is connected to tubing 174 which leads to a second or middle cassette 94b. The tubing 174 is connected, through the middle cassette 94b, to additional tubing 176, which includes a container access device 178 (e.g., a sharpened cannula or spike connector) for accessing the interior of a container, which may be an anticoagulant container in the case of a blood treatment operation. During a blood treatment operation (e.g., an MNC collection procedure), anticoagulant from the anticoagulant container is added to the blood from the fluid source at the y-connector 172 prior to entering the left cassette 94a.

The other fluid source access device 166 is used to deliver or return the original drawn fluid, a component of that fluid, and/or some other fluid to the fluid source (or to some other fluid recipient) and is also connected to the left cassette 94a through a y-connector 180. The other leg of the y-connector 180 is connected to tubing 182 in fluid communication at its other end with a container access device 184. Although not illustrated, the container access device 184 may be associated with a container having an amount of fluid (e.g., saline) to be used to prime the fluid flow circuit 12 and/or delivered to the fluid source (or some other fluid recipient) via the fluid source access device 166.

The left cassette 94a is also connected to tubing 186 in fluid communication with the separation chamber 22, which separates the fluid into its constituent parts and returns the fluid components to the fluid flow circuit 12, as described above. One of the fluid components (which may be separated red blood cells in an MNC collection procedure) is conveyed to the middle cassette 94b from the separation chamber 22 via tubing 188, while another separated component (which may be a plasma constituent in an MNC collection procedure) is conveyed to a third or right cassette 94c of the fluid flow circuit 12 from the separation chamber 22 via tubing 92. The first separated component (e.g., red blood cells) may be pumped to the left cassette 94a via tubing 190, where it is returned to the fluid source (or to some other fluid recipient), or may instead exit the middle cassette 94b via tubing 192 to a collection container 194 (referred to as a red blood cell collection container, in the context of a blood separation procedure) for storage or later use or may be recirculated from the middle cassette 94b through the separation chamber 22, as described above. The second separated component (e.g., the plasma constituent) may be pumped back to the left cassette 94a via tubing 196 for return to the fluid source (or to some other fluid recipient) and/or it may be pumped into a collection container 198 (referred to as a plasma collection container, in the context of a blood separation procedure) via different tubing 200 or recirculated from the right cassette 94c through the separation chamber 22, as described above. The destinations of the various fluids passing through the cassettes depends upon the actuation of the various valves of the cassettes 94, as described in greater detail in U.S. Pat. No. 5,462,416, which is incorporated herein by reference.

Each illustrated cassette 94 includes an injection-molded body that is compartmentalized by an interior wall to present or form a topside (which faces away from the separation assembly 10, during use) and an underside (which faces toward the separation assembly 10, during use). A flexible diaphragm overlies and peripherally seals the underside of each cassette 94, while a generally rigid upper panel overlies the topside of each cassette 94 and is sealed peripherally and to raised, channel-defining walls in the cassette 94.

The top- and undersides of the cassettes 94 contain preformed cavities. On the underside of the cassettes 94, the cavities form an array of valve stations and an array of pressure sensing stations. On the topside of the cassettes 94, the cavities form an array of channels or paths for conveying fluids. The valve stations communicate with the flow paths through the interior wall to interconnect them in a predetermined manner. The sensing stations also communicate with the flow paths through the interior wall to sense pressures in selected regions. The number and arrangement of the flow paths, the valve stations, and the sensing stations can vary without departing from the scope of the present disclosure.

In the illustrated embodiment, ten pre-molded tube connectors extend out along opposite side edges of each cassette 94. The tube connectors are arranged five on one side edge and five on the other side edge. The other side edges of the cassettes 94, as illustrated, are free of tube connectors. The tube connectors are associated with external tubing to associate the cassettes 94 with the remainder of the fluid flow circuit 12 (e.g., to a plasma collection container 198, an MNC collection container 202, or a red blood cell collection container 194) or to define tubing loops 204 that interact with pumps 90 of the separation assembly 10 to convey fluid through the fluid flow circuit 12, as described in greater detail in U.S. Pat. No. 5,462,416.

The tube connectors communicate with various interior flow paths, which constitute the flow paths of the cassettes 94 through which a fluid enters or exits the cassette 94. The remaining interior flow paths of the cassette 94 constitute branch paths that link the flow paths associated with the tube connectors to each other through the valve stations and sensing stations. The particular configuration of one suitable cassette is described in greater detail in U.S. Pat. No. 5,462,416.

The fluid flow circuit 12 may also include a number of other components, including clamps or valves, an air detector 206, and a drip chamber 208 that fluid passes through before entering the separation chamber 22.

As described above, the colorimetric optical sensor device 72 may be oriented to monitor fluid in any optically appropriate portion or vessel of the fluid flow circuit 12 (i.e., any portion or vessel in which fluid may be present and which is configured to allow for the passage of broadband light). This may include one of the tubes or conduits through which fluid flows, one of the cassettes, one of the containers, and the separation chamber 22. For example, FIG. 12 shows the colorimetric optical sensor device 72 positioned to monitor a vessel associated with the left cassette 94a, which may be advantageous for determining a main wavelength (and, hence, the hematocrit) of anticoagulated whole blood.

Figure 34:
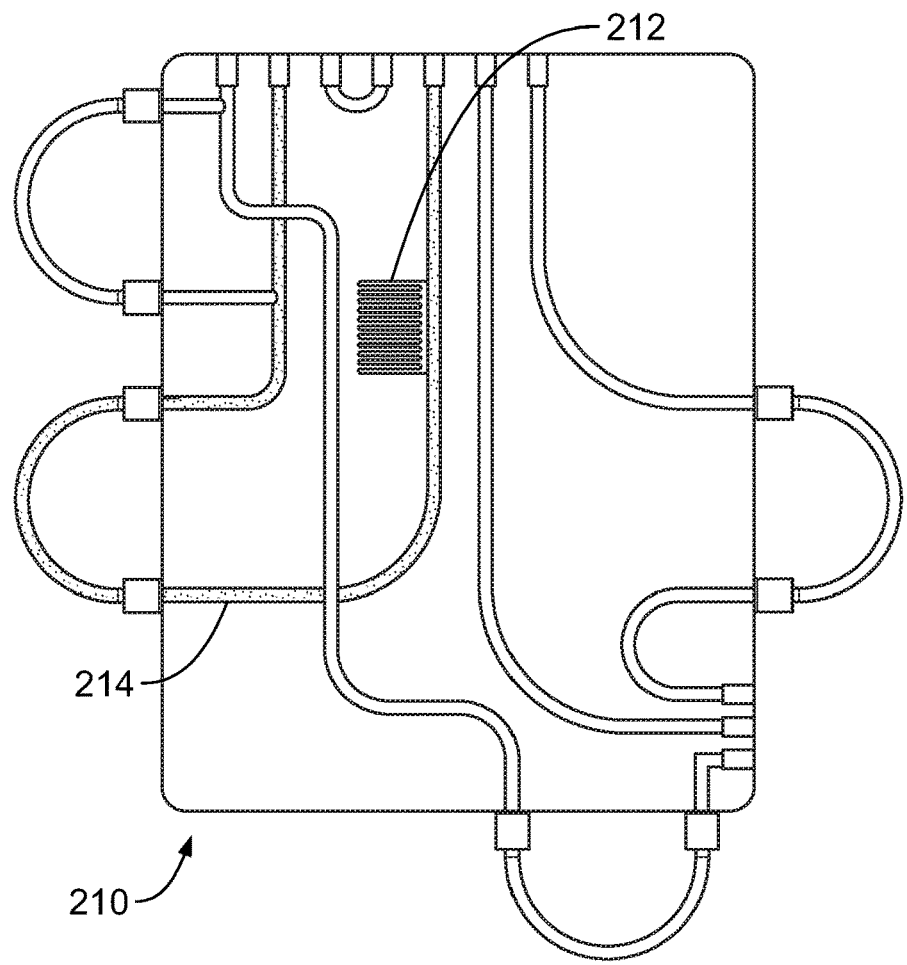
FIG. 34 is a top plan view of a cassette including a vessel or portion configured to be monitored by a colorimetric optical sensor device.
Figure 35:
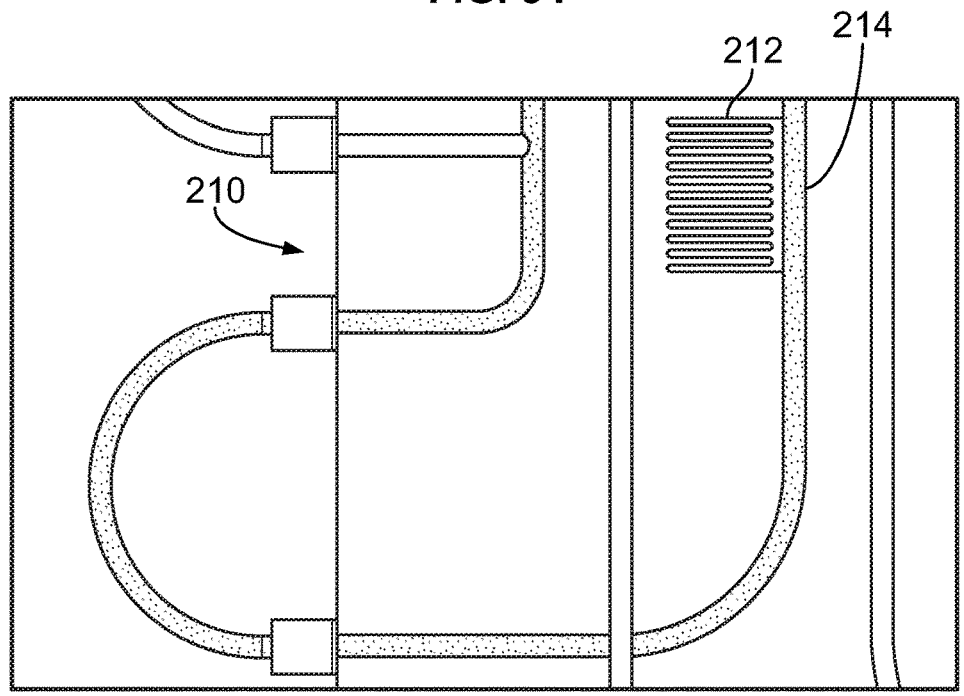
FIG. 35 is a top plan view of a portion of the cassette of FIG. 34.
Figure 36:
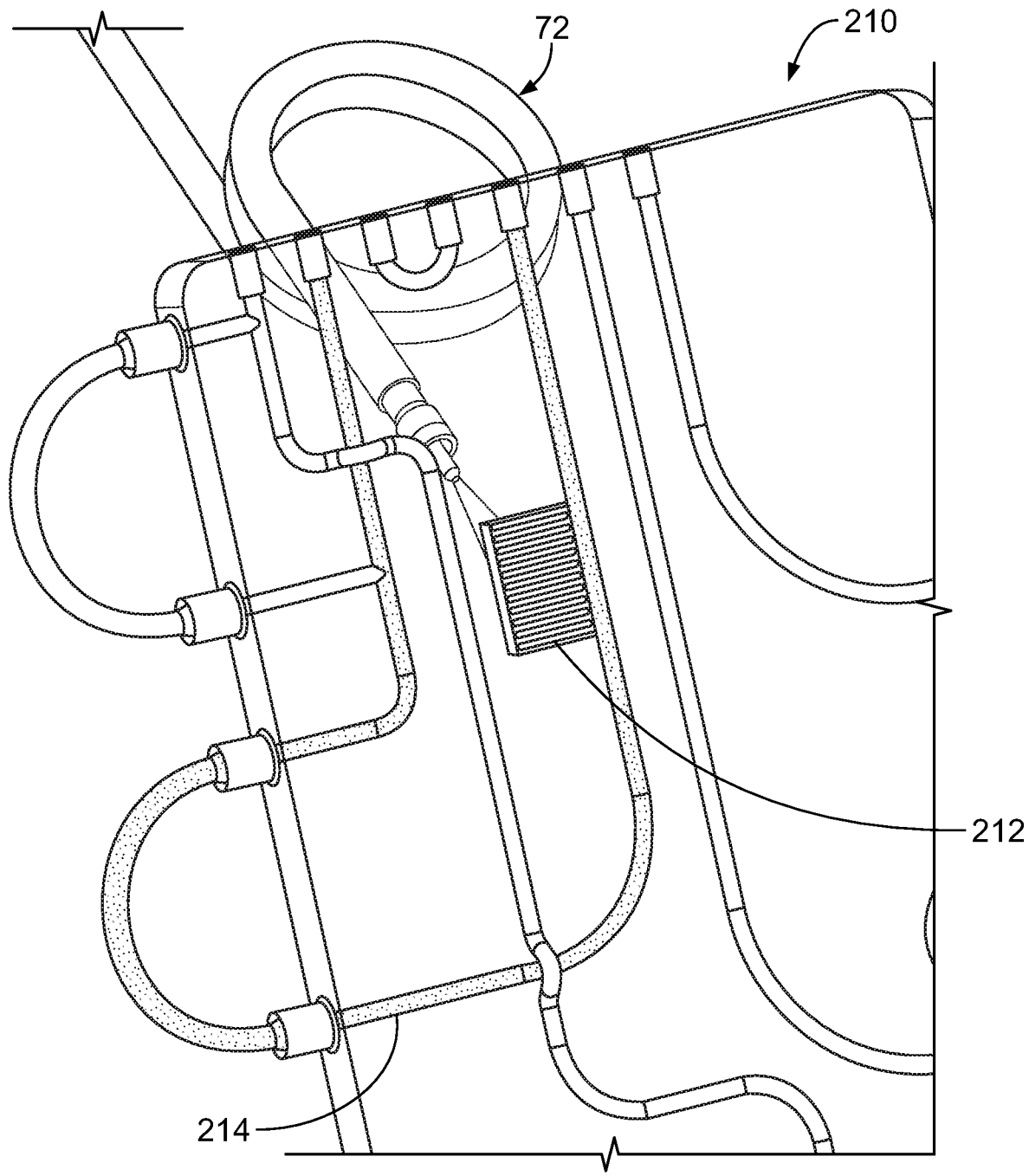
FIG. 36 is a perspective view of a portion of the cassette of FIG. 34 and an associated colorimetric optical sensor device.

FIGS. 34-36 show an exemplary cassette 210 including a vessel 212 that is subject to monitoring by a colorimetric optical sensor device 72, with FIG. 36 also showing a portion of an associated colorimetric optical sensor device 72. The colorimetric optical sensor device 72 may be oriented to observe the vessel 212 through the topside of the cassette 210 or through the underside of the cassette 210 (i.e., through a rigid upper panel or molded portion of the cassette 210 or through the flexible diaphragm of the cassette 210) or even through a side edge of the cassette 210. While FIGS. 34-36 show the vessel 212 configured as an optical mixing vessel (e.g., of the type shown in FIG. 21), it should be understood that the vessel may be differently configured, such as comprising a portion of the cassette that is configured for fluid flow, but not for optical mixing. The vessel 212 may be separately formed and associated with the cassette 210 (such as by bonding or otherwise securing at least a portion of the vessel 212 within a cavity defined in the cassette 210) or may instead be incorporated into the cassette 210 (such as by being formed via injection molding when the body of the cassette 210 is being formed).

The optical mixing vessel 212 of FIGS. 34-36 is shown as branching off from a channel 214 defined in the cassette 210, rather than being inline with the main path of the fluid through the cassette 210. By such a configuration, a portion of the fluid flowing through the channel 214 will flow into and through the fluid compartment of the vessel 212 (before returning to the channel 214 at an outlet of the fluid compartment) while the remainder of the fluid continues flowing through the channel 214. This may be preferred to configuring an optical mixing vessel so as to require all of the fluid to pass through the fluid compartment of the vessel, as such an inline configuration may tend to decrease the rate at which the fluid passes through the cassette 210. However, it should be understood that it is within the scope of the present disclosure for an optical mixing vessel to be configured so as to require all of the fluid to pass through its fluid compartment, which may be advantageous if it is considered necessary for all of the fluid to be monitored by the associated colorimetric optical sensor device 72. In yet another embodiment, if the optical mixing vessel 212 is configured as a branch off of a main flow channel 214 (as in FIGS. 34-36), the cassette 210 may be provided with at least one valve or clamp or similar fluid control device to selectively allow fluid to flow into the fluid compartment of the vessel 212 from the channel 214 and then prevent further flow of fluid into the vessel 212 from the channel 214. By such a configuration, the colorimetric optical sensor device 72 would observe stationary fluid within the vessel 212, rather than observing fluid flowing through the vessel 212. The process of filling the vessel 212, analyzing the fluid, and then emptying fluid from the vessel 212 may be periodically repeated during the procedure (e.g., every five minutes) to monitor the status of the fluid throughout the procedure without having to continuously flow the fluid through the vessel 212.

In addition to the colorimetric optical sensor device 72 and the vessel being suitable for positioning at various locations, it should also be understood that the separation assembly 10 may include a plurality of colorimetric optical sensor devices 72, with each one being configured to be associated with a different portion or vessel of the fluid flow circuit 12. Finally, it should be understood that the optical mixing techniques described herein are not limited to monitoring of any particularly configured vessel or fluid, but may be applied to any optically appropriate vessel and to any fluid.

Aspects

Aspect 1. A method of determining a characteristic of a fluid, comprising: providing a vessel including a fluid compartment and a contrast compartment positioned directly adjacent to the fluid compartment; providing a fluid having a fluid color with a main wavelength in the fluid compartment; configuring the contrast compartment to have a contrast color with a known main wavelength different from the main wavelength of the fluid color; exposing at least a portion of the vessel to a light emitted by a broadband light source so as to cause at least a portion of the light to be reflected by the fluid compartment and the contrast compartment; receiving at least a portion of the reflected light; analyzing at least a portion of the received light to determine a main wavelength of said at least a portion of the received light; and determining a characteristic of the fluid based at least in part on the main wavelength of the received light, the main wavelength of the contrast color, and the percentage of said at least a portion of the vessel occupied by the fluid compartment.

Aspect 2. The method of Aspect 1, wherein the fluid compartment comprises a channel including a plurality of elongated, fluidly connected, and substantially parallel rows, and the contrast compartment comprises a plurality of elongated, substantially parallel rows alternating with the rows of the channel.

Aspect 3. The method of Aspect 2, wherein a width of each row of the channel is equal to a width of each row of the contrast compartment.

Aspect 4. The method of Aspect 2, wherein a width of each row of the channel is different from a width of each row of the contrast compartment.

Aspect 5. The method of Aspect 1, wherein the fluid compartment comprises a plurality of isolated regions, and the contrast compartment comprises a plurality of isolated regions alternating with the isolated regions of the fluid compartment.

Aspect 6. The method of any one of the preceding Aspects, wherein said configuring the contrast compartment to have a contrast color with a known main wavelength different from the main wavelength of the fluid color includes providing a contrast fluid in the contrast compartment.

Aspect 7. The method of any one of Aspects 1-5, wherein said configuring the contrast compartment to have a contrast color with a known main wavelength different from the main wavelength of the fluid color includes omitting a contrast fluid from the contrast compartment.

Aspect 8. The method of any one of the preceding Aspects, wherein the fluid color has a higher main wavelength than the contrast color.

Aspect 9. The method of any one of the preceding Aspects, wherein the fluid comprises a biological fluid having a hematocrit greater than 20%, and the main wavelength of said at least a portion of the received light is indicative of a hematocrit less than 20%.

Aspect 10. The method of any one of Aspects 1-7, wherein the fluid color has a lower main wavelength than the contrast color.

Aspect 11. A system for determining a characteristic of a fluid, comprising a vessel including a fluid compartment configured to receive a fluid having a fluid color with a main wavelength, and a contrast compartment positioned directly adjacent to the fluid compartment and configured to have a contrast color with a known main wavelength different from the main wavelength of the fluid color; and a colorimetric optical sensor device comprising a broadband light source configured to emit a light, with at least a portion of the light being exposed to at least a portion of the vessel and reflected by the fluid compartment and the contrast compartment, an optical spectrometer configured to receive at least a portion of the reflected light and analyze at least a portion of the received light to determine a main wavelength of said at least a portion of the received light, and a controller configured to determine a characteristic of the fluid based at least in part on the main wavelength of the received light, the main wavelength of the contrast color, and the percentage of said at least a portion of the vessel occupied by the fluid compartment.

Aspect 12. The system of Aspect 11, wherein the fluid compartment comprises a channel including a plurality of elongated, fluidly connected, and substantially parallel rows, and the contrast compartment comprises a plurality of elongated, substantially parallel rows alternating with the rows of the channel.

Aspect 13. The system of Aspect 12, wherein a width of each row of the channel is equal to a width of each row of the contrast compartment.

Aspect 14. The system of Aspect 12, wherein a width of each row of the channel is different from a width of each row of the contrast compartment.

Aspect 15. The system of Aspect 11, wherein the fluid compartment comprises a plurality of isolated regions, and the contrast compartment comprises a plurality of isolated regions alternating with the isolated regions of the fluid compartment.

Aspect 16. The system of any one of Aspects 11-15, wherein the contrast compartment contains a contrast fluid.

Aspect 17. The system of any one of Aspects 11-15, wherein the contrast compartment does not contain a contrast fluid.

Aspect 18. The system of any one of Aspects 11-17, wherein the vessel comprises a microfluidic chip.

Aspect 19. The system of any one of Aspects 11-18, further comprising a cassette defining a cavity receiving at least a portion of the vessel.

Aspect 20. The system of any one of Aspects 11-17, further comprising a cassette including a molded body, wherein the fluid compartment is molded into the body of the cassette.

Aspect 21. A vessel for changing the apparent color of a fluid, comprising a fluid compartment configured to receive a fluid having a fluid color with a main wavelength, and a contrast compartment positioned directly adjacent to the fluid compartment and configured to have a contrast color with a known main wavelength different from the main wavelength of the fluid color.

Aspect 22. The vessel of Aspect 21, wherein the fluid compartment comprises a channel including a plurality of elongated, fluidly connected, and substantially parallel rows, and the contrast compartment comprises a plurality of elongated, substantially parallel rows alternating with the rows of the channel.

Aspect 23. The vessel of Aspect 22, wherein a width of each row of the channel is equal to a width of each row of the contrast compartment.

Aspect 24. The vessel of Aspect 22, wherein a width of each row of the channel is different from a width of each row of the contrast compartment.

Aspect 25. The vessel of Aspect 21, wherein the fluid compartment comprises a plurality of isolated regions, and the contrast compartment comprises a plurality of isolated regions alternating with the isolated regions of the fluid compartment.

Aspect 26. The vessel of any one of Aspects 21-25, wherein the contrast compartment contains a contrast fluid.

Aspect 27. The vessel of any one of Aspects 21-25, wherein the contrast compartment does not contain a contrast fluid.

Aspect 28. The vessel of any one of Aspects 21-27, wherein the vessel comprises a microfluidic chip.

Aspect 29. The vessel of any one of Aspects 21-28, further comprising a cassette defining a cavity receiving at least a portion of the vessel.

Aspect 30. The vessel of any one of Aspects 21-27, wherein the fluid compartment is defined in a molded body of a cassette.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A system for determining a characteristic of a fluid, comprising
a vessel including
a fluid compartment configured to receive a fluid having a fluid color with a main wavelength, and
a contrast compartment positioned directly adjacent to the fluid compartment and configured to have a contrast color with a known main wavelength different from the main wavelength of the fluid color; and
a colorimetric optical sensor device comprising
a broadband light source configured to emit a light, with at least a portion of the light being exposed to at least a portion of the vessel and reflected by the fluid compartment and the contrast compartment,
an optical spectrometer configured to receive at least a portion of the reflected light and analyze at least a portion of the received light to determine a main wavelength of said at least a portion of the received light, and
a controller configured to determine a characteristic of the fluid based at least in part on the main wavelength of the received light, the main wavelength of the contrast color, and the percentage of said at least a portion of the vessel occupied by the fluid compartment.

2. The system of claim 1, wherein
the fluid compartment comprises a channel including a plurality of elongated, fluidly connected, and substantially parallel rows, and
the contrast compartment comprises a plurality of elongated, substantially parallel rows alternating with the rows of the channel.

3. The system of claim 2, wherein a width of each row of the channel is equal to a width of each row of the contrast compartment.

4. The system of claim 2, wherein a width of each row of the channel is different from a width of each row of the contrast compartment.

5. The system of claim 1, wherein
the fluid compartment comprises a plurality of isolated regions, and
the contrast compartment comprises a plurality of isolated regions alternating with the isolated regions of the fluid compartment.

6. The system of claim 1, wherein the contrast compartment contains a contrast fluid.

7. The system of claim 1, wherein the contrast compartment does not contain a contrast fluid.

8. The system of claim 1, wherein the vessel comprises a microfluidic chip.

9. The system of claim 1, further comprising a cassette defining a cavity receiving at least a portion of the vessel.

10. The system of claim 1, further comprising a cassette including a molded body, wherein the fluid compartment is molded into the body of the cassette.

11. A fluid flow circuit, comprising:
a main flow channel defining a portion of a fluid flow path; and
a vessel for changing the apparent color of a fluid flowing through the main flow channel and having a fluid color with a main wavelength, the vessel branching off from the main flow channel and comprising
a fluid compartment configured to receive a portion of the fluid, flowing through the main flow channel, and
a contrast compartment positioned directly adjacent to the fluid compartment and configured to have a contrast color with a known main wavelength different from the main wavelength of the fluid color.

12. The fluid flow circuit of claim 11, wherein
the fluid compartment comprises a vessel channel including a plurality of elongated, fluidly connected, and substantially parallel rows, and
the contrast compartment comprises a plurality of elongated, substantially parallel rows alternating with the rows of the vessel channel.

13. The fluid flow circuit of claim 12, wherein a width of each row of the vessel channel is equal to a width of each row of the contrast compartment.

14. The fluid flow circuit of claim 12, wherein a width of each row of the vessel channel is different from a width of each row of the contrast compartment.

15. The fluid flow circuit of claim 11, wherein the fluid compartment comprises a plurality of isolated regions, and the contrast compartment comprises a plurality of isolated regions alternating with the isolated regions of the fluid compartment.

16. The fluid flow circuit of claim 11, wherein the contrast compartment contains a contrast fluid.

17. The fluid flow circuit of claim 11, wherein the contrast compartment does not contain a contrast fluid.

18. The fluid flow circuit of claim 11, wherein the vessel comprises a microfluidic chip.

19. The fluid flow circuit of claim 11, wherein the main flow channel is at least partially defined a cassette, and the cassette defines a cavity receiving at least a portion of the vessel.

20. The fluid flow circuit of claim 11, wherein the fluid compartment and at least a portion of the main flow channel are is defined in a molded body of a cassette.

\* \* \* \* \*